(12) United States Patent
Varsavsky et al.

(10) Patent No.: US 10,478,557 B2
(45) Date of Patent: *Nov. 19, 2019

(54) PERSONALIZED PARAMETER MODELING METHODS AND RELATED DEVICES AND SYSTEMS

(71) Applicant: MEDTRONIC MINIMED, INC., Northridge, CA (US)

(72) Inventors: Andrea Varsavsky, Santa Monica, CA (US); Yunfeng Lu, Granada Hills, CA (US); Keith Nogueira, Mission Hills, CA (US); Jeffrey Nishida, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 431 days.

This patent is subject to a terminal disclaimer.

(21) Appl. No.: 15/240,726

(22) Filed: Aug. 18, 2016

(65) Prior Publication Data
US 2017/0049963 A1 Feb. 23, 2017

Related U.S. Application Data

(60) Provisional application No. 62/208,445, filed on Aug. 21, 2015.

(51) Int. Cl.
*G01N 33/48* (2006.01)
*A61M 5/172* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS

| 3,631,847 A | 1/1972 | Hobbs, II |
| 4,212,738 A | 7/1980 | Henne |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.
(Continued)

*Primary Examiner* — Larry D Riggs, II
(74) *Attorney, Agent, or Firm* — Lorenz & Kopf, LLP

(57) ABSTRACT

Medical devices and related patient management systems and parameter modeling methods are provided. An exemplary method of operating a sensing device associated with a patient involves obtaining current operational context information associated with the sensing device, obtaining a parameter model associated with the patient, calculating a current parameter value based on the parameter model and the current operational context information, obtaining one or more signals from a sensing element configured to measure a condition in a body of the patient, and providing an output that is influenced by the calculated current parameter value and the one or more signals.

20 Claims, 12 Drawing Sheets

(51) Int. Cl.

| | |
|---|---|
| *G06F 19/00* | (2018.01) |
| *A61B 5/145* | (2006.01) |
| *A61B 5/00* | (2006.01) |
| *G16H 10/60* | (2018.01) |
| *G16H 50/50* | (2018.01) |
| *G16H 40/63* | (2018.01) |
| *G16H 40/40* | (2018.01) |
| *G16H 50/20* | (2018.01) |
| *A61B 5/024* | (2006.01) |
| *A61M 5/142* | (2006.01) |
| *G16H 15/00* | (2018.01) |

(52) U.S. Cl.
CPC ......... *G06F 19/3468* (2013.01); *G16H 10/60* (2018.01); *G16H 40/40* (2018.01); *G16H 40/63* (2018.01); *G16H 50/20* (2018.01); *G16H 50/50* (2018.01); *A61B 5/0022* (2013.01); *A61B 5/02438* (2013.01); *A61B 5/7239* (2013.01); *A61B 5/7242* (2013.01); *A61B 2560/0242* (2013.01); *A61B 2562/0219* (2013.01); *A61M 5/14244* (2013.01); *A61M 2205/3569* (2013.01); *A61M 2205/502* (2013.01); *A61M 2205/52* (2013.01); *A61M 2205/70* (2013.01); *A61M 2230/005* (2013.01); *A61M 2230/06* (2013.01); *A61M 2230/201* (2013.01); *G16H 15/00* (2018.01)

(56) References Cited

U.S. PATENT DOCUMENTS

| | | | |
|---|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |

(56) References Cited

U.S. PATENT DOCUMENTS

| | | |
|---|---|---|
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,248,093 B1 | 6/2001 | Moberg |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,323,142 B2 | 1/2008 | Pendo et al. |
| 7,396,330 B2 | 7/2008 | Banet et al. |
| 7,402,153 B2 | 7/2008 | Steil et al. |
| 7,621,893 B2 | 11/2009 | Moberg et al. |
| 8,474,332 B2 | 7/2013 | Bente, IV |
| 8,674,288 B2 | 3/2014 | Hanson et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0031094 A1 | 2/2006 | Cohen et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |
| 2013/0338630 A1 | 12/2013 | Agrawal et al. |
| 2015/0057634 A1 | 2/2015 | Mastrototaro et al. |
| 2015/0057807 A1 | 2/2015 | Mastrototaro et al. |
| 2015/0130633 A1 | 5/2015 | Grubstein et al. |
| 2015/0164371 A1 | 6/2015 | Varsavsky et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |

(56) References Cited

FOREIGN PATENT DOCUMENTS

| WO | WO 2005/065538 A2 | 7/2005 |
|---|---|---|
| WO | WO 2008/089375 A1 | 7/2008 |

OTHER PUBLICATIONS (Animas Corporation, 1999). Animas . . . bringing new life to insulin therapy.
Bode B W, et al. (1996). Reduction in Severe Hypoglycemia with Long-Term Continuous Subcutaneous Insulin Infusion in Type I Diabetes. Diabetes Care, vol. 19, No. 4, 324-327.
Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch Ret al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting a Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed• Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-Tron® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.

(56) References Cited

OTHER PUBLICATIONS

Koudelka, M., et al., "Planar Amperometric Enzyme-Based Glucose Microelectrode," Sensors & Actuators, 18, 1989, pp. 157-165.

Mastrototaro, John J., et al., "An electroenzymatic glucose sensor fabricated on a flexible substrate," Sensors & Actuators, B. 5, 1991, pp. 139-144.

Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

Mckean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artificel endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas-Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

PERSONALIZED PARAMETER MODELING METHODS AND RELATED DEVICES AND SYSTEMS

CROSS-REFERENCE TO RELATED APPLICATION(S)

This application claims the benefit of U.S. Provisional Patent Application Ser. No. 62/208,445, filed Aug. 21, 2015.

TECHNICAL FIELD

Embodiments of the subject matter described herein relate generally to medical devices, and more particularly, embodiments of the subject matter relate to therapy management using personalized, patient-specific parameter models.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Control schemes have been developed that allow insulin infusion pumps to monitor and regulate a user's blood glucose level in a substantially continuous and autonomous manner. However, regulating blood glucose level is still complicated by variations in a user's individual insulin response and daily activities (e.g., exercise, carbohydrate consumption, bolus administration, and the like) in conjunction with variations associated with the devices or components used to implement continuous glucose monitoring and related controls, and potentially other factors that may contribute to variations, uncertainty, or otherwise impair accuracy or reliability. Since many of the variables influencing glucose regulation and control are dynamically or periodically changing, practical realities dictate that some variables likely will not be optimal at all times. Accordingly, there is a need to account for potential variables in a manner that improves performance and patient outcomes.

BRIEF SUMMARY

Medical devices and related systems and operating methods are provided. An embodiment of a method of operating a sensing device associated with a patient involves obtaining current operational context information associated with the sensing device, obtaining a parameter model associated with the patient, calculating a current parameter value based on the parameter model and the current operational context information, obtaining one or more signals from a sensing element configured to measure a condition in a body of the patient, and providing an output that is influenced by the calculated current parameter value and the one or more signals.

In another embodiment, an apparatus for a sensing device is provided. The sensing device includes a sensing element to obtain one or more measurement signals influenced by a physiological condition of a patient, a data storage element to store a parameter model associated with the patient, an output interface, and a control module coupled to the sensing element, the data storage element, and the output interface to calculate a current parameter value based on the parameter model and current operational context information and provide an output at the output interface that is influenced by the calculated current parameter value and the one or more measurement signals.

In another embodiment, a system is provided that includes a computing device communicatively coupled to a network to obtain historical operational context information associated with a patient via the network, obtain historical values for a parameter associated with the patient via the network, and determine a patient-specific model for the parameter based on a relationship between the historical operational context information and the historical values. The system also includes a sensing device communicatively coupled to the computing device to obtain the patient-specific model, obtain current operational context information associated with the sensing device, calculate a current value for the parameter based on the patient-specific model and the current operational context information, obtain one or more signals influenced by a condition in a body of the patient from a sensing element of the sensing device, and generate an output that is influenced by the calculated current parameter value and the one or more signals.

Another embodiment of a method is provided that involves obtaining, by a computing device, historical measurements of a condition in a body of the patient previously provided by a sensing device, obtaining, by the computing device, historical operational context information associated with preceding operation of one or more of an infusion device and the sensing device, obtaining, by the computing device, historical values for a parameter from one or more of the infusion device and the sensing device, determining, by the computing device a patient-specific model of the parameter based on relationships between the historical measurements, the historical operational context information and the historical values, and providing, by the computing device via a network, the patient-specific model to one of the infusion device, the sensing device or a client device, wherein subsequent operation of the one of the infusion device, the sensing device, or the client device is influenced by the patient-specific model.

In another embodiment, a system is provided that includes a database to store historical measurements of a condition in a body of a patient, historical delivery information for fluid influencing the condition previously delivered to the body of the patient, historical operational context information associated with the patient, and historical values for a parameter associated with the patient. The system also includes a remote server coupled to the database and a network to determine a patient-specific model of the parameter based on relationships between the historical measurements, the historical delivery information, the historical operational context information and the historical values and provide the patient-specific model to a computing device via the network.

In yet another embodiment, a system is provided that includes a sensing device communicatively coupled to a network and configured to obtain measurements of a condition in a body of a patient, a database to store historical measurements of the condition in the body of the patient from the sensing device, historical operational context information associated with the patient, and historical values for a parameter associated with the patient, and a remote server coupled to the database and a network to determine a patient-specific model of the parameter based on relationships between the historical measurements, the historical operational context information and the historical values and provide the patient-specific model to the sensing device via the network, wherein subsequent output from the sensing device is influenced by the patient-specific model.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
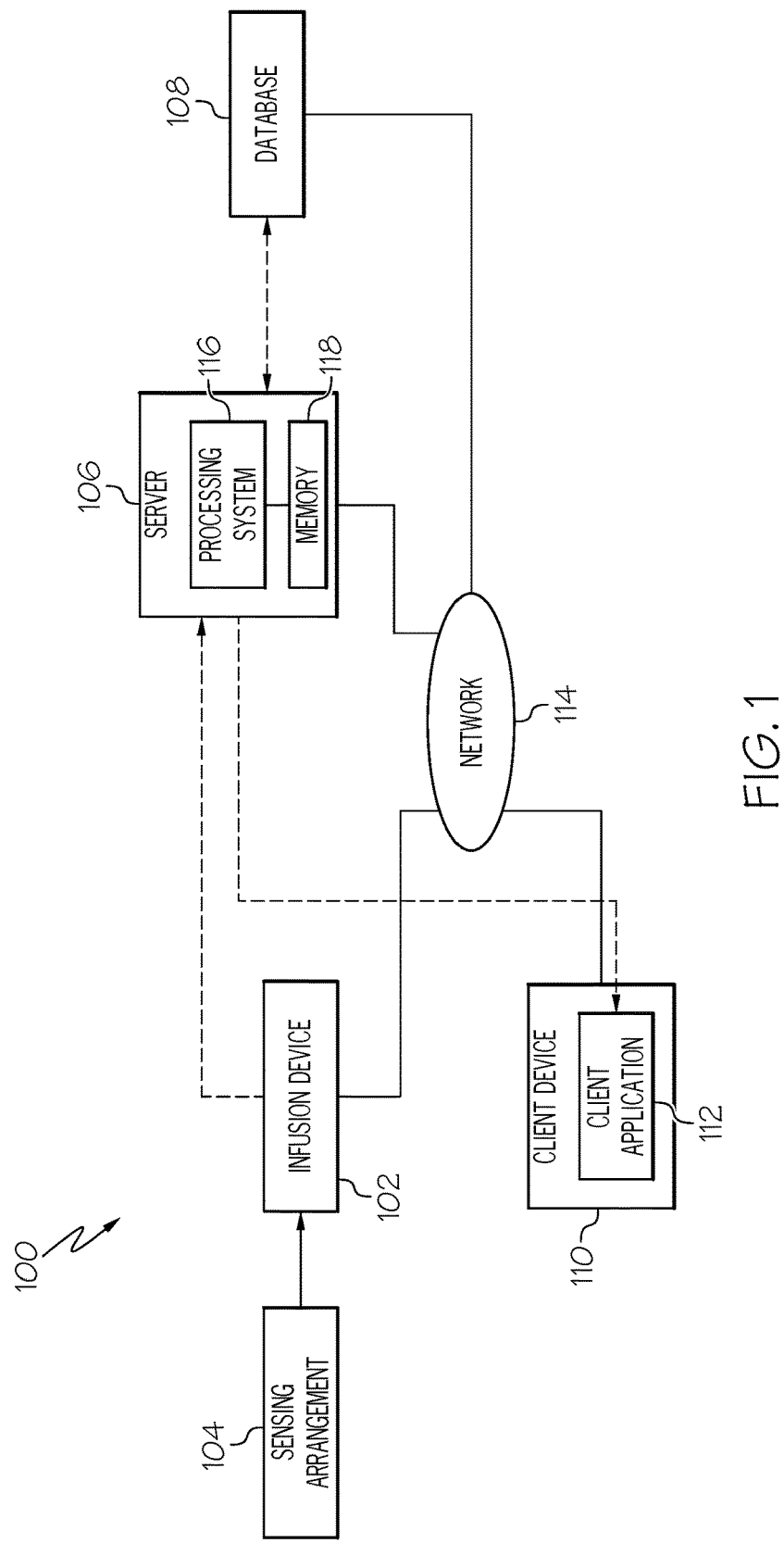
FIG. 1 depicts an exemplary embodiment of a patient management system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference. That said, the subject matter described herein can be utilized more generally in the context of overall diabetes management or other physiological conditions independent of or without the use of an infusion device or other medical device (e.g., when oral medication is utilized), and the subject matter described herein is not limited to any particular type of medication.

Generally, a fluid infusion device includes a motor or other actuation arrangement that is operable to linearly displace a plunger (or stopper) of a reservoir provided within the fluid infusion device to deliver a dosage of fluid, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Exemplary embodiments described herein generally relate to systems for modeling control parameters or variables in a manner that improves component performance, systemic performance, user experience, and/or the like, an in particular, in conjunction with operation of a medical device, such as, for example, operation of a sensing arrangement (or sensing device) to monitor a physiological condition in a body of a patient or operation of an infusion device delivering fluid influencing the physiological condition to the body of the patient. In this regard, the current values utilized for such parameters or variables may be determined dynamically or in real-time using the corresponding model to account for the current operational context experienced by the respective device. In exemplary embodiments, the parameter models are personalized and patient-specific, and rely on input variables indicative of the current operational context that have been identified as predictive or correlative to the value of that parameter based on historical data associated with the patient. In this regard, for each patient, the particular subset of input variables that are predictive or correlative to a particular parameter for that patient may be different from those of other patients.

In one or more exemplary embodiments, patient-specific models are utilized to calculate or otherwise determine factors used to convert a measurement signal to a corresponding calibrated measurement value, such as a calibrated glucose measurement value. For example, the calibration factor used to convert from a measurement signal to a calibrated glucose measurement value may be determined based at least in part on one or more of a current location of the sensing arrangement (or sensor site location) on the body of the patient, the number or type of sensing arrangements being utilized, current measurements from other sensing arrangements, one or more current temporal variables (e.g., current time of day, day of week, month of year, etc.), one or more current environmental or geographic variables, patient demographics, and/or current patient variables (e.g., the patient's current weight, body mass index, or the like). Thus, the calibration factor may vary over time as dictated by different operational contexts, and in a unique patient-specific manner. Similarly, the amount of offset to be applied to the measurement signal before conversion may be determined dynamically or in real-time and in a patient-specific manner using a corresponding model.

Additionally, in some embodiments, patient-specific models are utilized to generate user notifications, alerts or indications or generate graphical user interface (GUI) displays. For example, a patient-specific model may be utilized to determine one or more optimal or recommended times of day for the patient to calibrate a sensing arrangement and provide corresponding indications or guidance to the patient. Similarly, a patient-specific model may be utilized to determine one or more optimal or recommended sensor site locations on the body for the sensing arrangement and provide corresponding indications or guidance to the patient. In this regard, a sensor site (or site), site location, or variants thereof should be understood as referring to a distinct region of the body where a sensing arrangement may be attached, inserted, affixed, or otherwise located. It should also be noted that different sites may be associated with a common part of the body (e.g., the abdomen) while being physically distinguishable (e.g., different sides of the body, different quadrants or sectors of a body part, or the like). In some embodiments, patient-specific models are also utilized to calculate or otherwise determine one or more metrics indicative of the health or useful life of the sensing arrangement and provide corresponding indications or guidance to the patient. Additionally, in some embodiments, patient-specific models may be utilized to dynamically adjust one or more aspects of the control scheme being implemented by changing the values of control parameters or the like relied on by the control scheme.

FIG. 1 depicts an exemplary embodiment of a patient management system 100. The patient management system 100 includes an infusion device 102 that is communicatively coupled to a sensing arrangement 104 to obtain measurement data indicative of a physiological condition in the body of a patient, such as sensor glucose measurement values, as described in greater detail below in the context of FIGS. 5-10. In one or more exemplary embodiments, the infusion device 102 operates autonomously to regulate the patient's glucose level based on the sensor glucose measurement values received from the sensing arrangement 104.

In the illustrated embodiment, the infusion device 102 periodically uploads or otherwise transmits the measurement data (e.g., sensor glucose measurement values and timestamps associated therewith) to a remote device 106 via a communications network 114, such as a wired and/or wireless computer network, a cellular network, a mobile broadband network, a radio network, or the like. That said, in other embodiments, the sensing arrangement 104 may be communicatively coupled to the communications network 114 to periodically upload or otherwise transmit measurement data to the remote device 106 via the communications network 114 independent of the infusion device 102. While FIG. 1 depicts a single sensing arrangement 104, in practice, embodiments of the system 100 may include multiple different sensing arrangements, which may be configured to sense, measure, or otherwise quantify any number of conditions or characteristics. For example, multiple instances of a glucose sensing arrangement 104 may be deployed for redundancy or other purposes (e.g., averaging or other statistical operations). In other embodiments, additional sensing arrangements 104 may be deployed to measure different physiological conditions of the patient, such as, for example, the patient's heart rate, oxygen levels, or the like.

In exemplary embodiments, the infusion device 102 also uploads delivery data and/or other information indicative of the amount of fluid delivered by the infusion device and the timing of fluid delivery, which may include, for example, information pertaining to the amount and timing of manually-initiated boluses and associated meal announcements. Some examples of an infusion device uploading measurement and delivery data to a remote device are described in United States Patent Application Publication Nos. 2015/0057807 and 2015/0057634, which are incorporated by reference herein in their entirety. In addition to measurement and delivery data, various control parameter values of the sensing arrangement 104 and/or the infusion device 102 (e.g., calibration factors, sensitivity factors, and the like) may also be uploaded to the remote device 106.

The information uploaded to the remote device 106 by the infusion device 102 and/or the sensing arrangement 104 may also include operational context information, such as, for example, geographic location data associated with the infusion device 102 and/or the sensing arrangement 104, data pertaining to environmental conditions (e.g., temperature, humidity, or the like) at the geographic location or in the vicinity of the infusion device 102 and/or the sensing arrangement 104, and other data characterizing or describing the current operational context for the infusion device 102 and/or the sensing arrangement 104. Additionally, current or updated patient data may be uploaded to the remote device 106, such as, for example, the current weight of the patient, the height of the patient, the current body mass index of the patient, or the like. In some embodiments, activity or behavioral data for the patient may also be uploaded, such as, for example, indications of the type and duration of exercise or other activity undertaken by the patient. The uploaded information may also include gender information, age information, and other demographic information associated with the patient.

The remote device 106 generally represents a computing system or another combination of processing logic, circuitry, hardware, and/or other components configured to support the processes, tasks, operations, and/or functions described herein. In this regard, the server 106 includes a processing system 116, which may be implemented using any suitable processing system and/or device, such as, for example, one or more processors, central processing units (CPUs), controllers, microprocessors, microcontrollers, processing cores and/or other hardware computing resources configured to support the operation of the processing system 116 described herein. The processing system 116 may include or otherwise access a data storage element 118 (or memory) capable of storing programming instructions for execution by the processing system 116, that, when read and executed, cause processing system 116 to perform or otherwise support the processes, tasks, operations, and/or functions described herein. For example, in one embodiment, the instructions cause the processing system 116 to create, generate, or otherwise facilitate an application platform that supports instances of an application using data that is stored or otherwise maintained by the database 108. Depending on the embodiment, the memory 118 may be realized as a random access memory (RAM), read only memory (ROM), flash memory, magnetic or optical mass storage, or any other suitable non-transitory short or long term data storage or other computer-readable media, and/or any suitable combination thereof.

In exemplary embodiments, the remote device 106 is coupled to a database 108 configured to store or otherwise maintain historical measurement data, historical delivery data, historical control parameter data, and other uploaded operational context or demographic information corresponding to such data in association with a patient associated with the infusion device 102 and/or the sensing arrangement 104 (e.g., using unique patient identification information). Additionally, the database 108 may store or otherwise maintain, in association with a particular patient, personalized and patient-specific control parameter models. In this regard, a control parameter model defines which input variables or parameters are to be factored in to calculate a resulting control parameter value along with relative weightings assigned to those respective inputs corresponding to how predictive or correlative the value of a respective model input value is to the control parameter value, as described in greater detail below in the context of FIG. 2. The remote device 106 generally represents an electronic device configured to analyze or otherwise monitor the measurement and delivery data obtained for the patient associated with the infusion device 102 and generate patient-specific control parameter models based on a respective patient's historical measurement, delivery, and control parameter data in conjunction with the historical operational context data and/or demographic data.

In some embodiments, the remote device 106 also generates or otherwise facilitates a GUI display that is influenced by or otherwise reflects a control parameter value determined using a corresponding model. The GUI display may be presented on the remote device 106 or another electronic device 110, alternatively referred to herein as a client device. In practice, the remote device 106 may reside at a location that is physically distinct and/or separate from the infusion device 102, such as, for example, at a facility that is owned and/or operated by or otherwise affiliated with a manufacturer of the infusion device 102. For purposes of explanation, but without limitation, the remote device 106 may alternatively be referred to herein as a server.

The client device 110 generally represents an electronic device coupled to the network 114, and in practice, the client device 110 can be realized as any sort of personal computer, mobile telephone, tablet or other network-enabled electronic device that includes a display device, such as a monitor, screen, or another conventional electronic display, capable of graphically presenting data and/or information provided by the server 106 along with a user input device, such as a keyboard, a mouse, a touchscreen, or the like, capable of receiving input data and/or other information from the user of the client device 110. In one or more embodiments, a user, such as the patient, the patient's doctor or another healthcare provider, or the like, manipulates the client device 110 to execute a client application 112 that contacts the server 106 via the network 114 using a networking protocol, such as the hypertext transport protocol (HTTP) or the like. The client application 112 may be utilized by a user to access and view data stored in the database 108 via the server 106, or otherwise receive information or indications pertaining to operations of the infusion device 102 and/or the sensing arrangement 104.

It should be appreciated that FIG. 1 depicts a simplified representation of a patient management system 100 for purposes of explanation and is not intended to limit the subject matter described herein in any way. For example, in various embodiments, one or more of the devices 102, 104, 106, 108, 110 may be absent from the system 100. For example, one or more of the infusion device 102, the sensing arrangement 104, or the client device 110 may be configured to perform the functionality described herein in the context of the remote device 106 and/or database 108, in which case the remote device 106 and/or the database 108 may not be present in such an embodiment.

Figure 2:
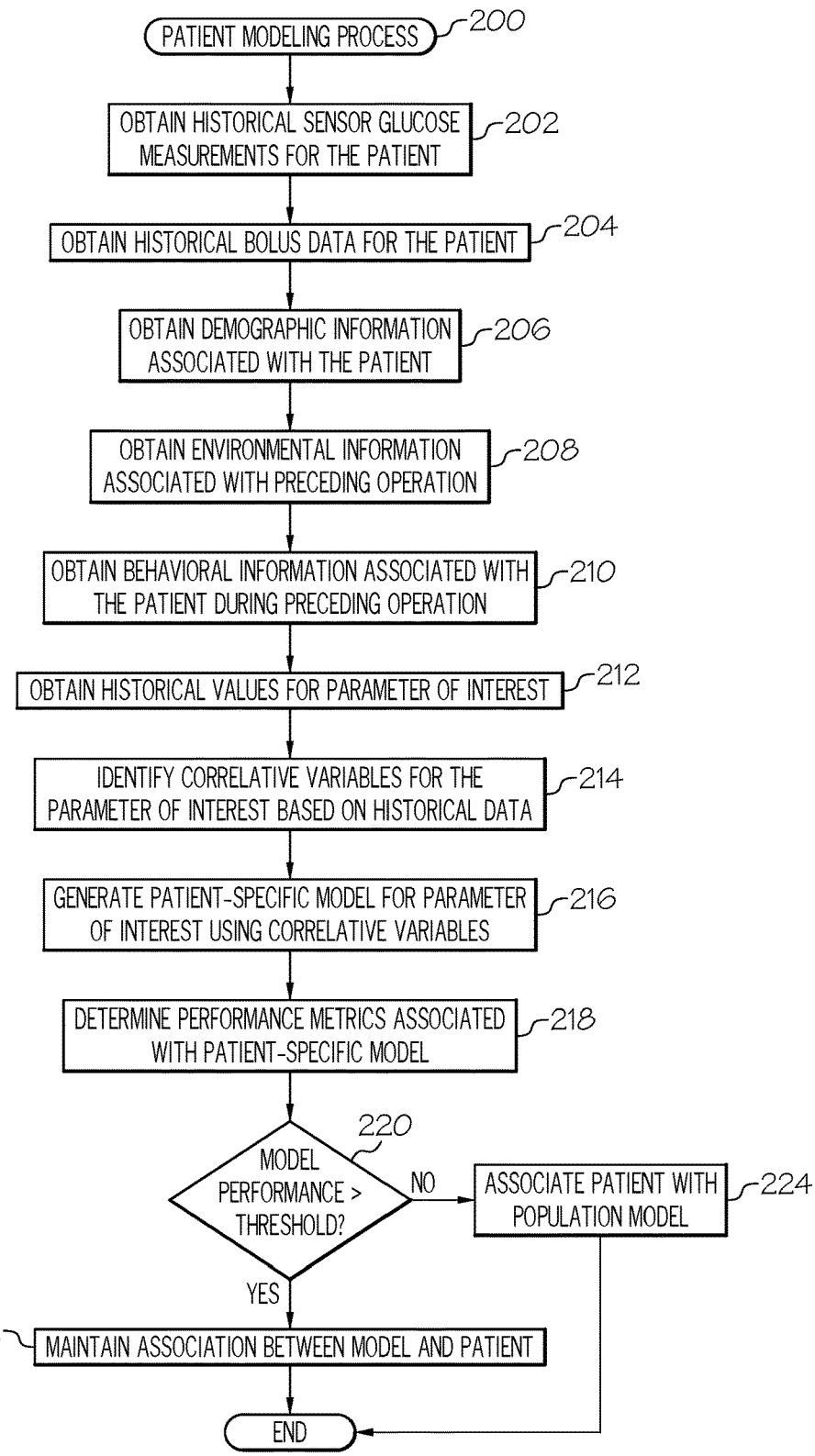
FIG. 2 is a flow diagram of an exemplary patient modeling process suitable for use with the patient management system of FIG. 1 in one or more exemplary embodiments.

FIG. 2 depicts an exemplary patient modeling process 200 suitable for implementation by a patient management system to develop a patient-specific control parameter model. The various tasks performed in connection with the patient modeling process 200 may be performed by hardware, firmware, software executed by processing circuitry, or any combination thereof. For illustrative purposes, the following description refers to elements mentioned above in connection with FIG. 1. In practice, portions of the patient modeling process 200 may be performed by different elements of the patient management system 100, such as, for example, the infusion device 102, the sensing arrangement 104, the server 106, the database 108, the client device 110, the client application 112, and/or the processing system 116. It should be appreciated that the patient modeling process 200 may include any number of additional or alternative tasks, the tasks need not be performed in the illustrated order and/or the tasks may be performed concurrently, and/or the patient modeling process 200 may be incorporated into a more comprehensive procedure or process having additional functionality not described in detail herein. Moreover, one or more of the tasks shown and described in the context of FIG. 2 could be omitted from a practical embodiment of the patient modeling process 200 as long as the intended overall functionality remains intact.

The patient modeling process 200 begins by obtaining historical measurement data for the patient of interest and obtaining historical bolus data for the patient over the period corresponding to the historical measurement data (tasks 202, 204). For example, the infusion device 102 may periodically upload, to the server 106 via the network 114, reference blood glucose measurement values obtained from the body of the patient (e.g., using a blood glucose meter or fingerstick device) along with bolus information including the timings and amounts of insulin delivered, including indications of whether a particular bolus is a meal bolus or otherwise associated with a meal. The bolus information may also include the amount of carbohydrates consumed, the type of meal, or the like. In this regard, in the absence of an explicit meal indication or announcement from the patient, the server 106 may automatically classify a bolus delivered as a meal bolus when a carbohydrate entry occurred within a threshold amount of time of the bolus being delivered (e.g., within 5 minutes). Additionally, the infusion device 102 (or alternatively, the sensing arrangement 104) may periodically upload, to the server 106, sensor glucose measurement values obtained from the body of the patient by the sensing arrangement 104. In exemplary embodiments, the historical measurement values may also be stored in association with a current location of the sensing arrangement 104 (or sensor site location) on the body of the patient at the time the respective measurement values were obtained.

The illustrated patient modeling process 200 also obtains demographic information or other clinically-relevant information associated with the patient (task 206). Demographic information associated with the patient may be input or otherwise provided by the patient or another user to any one of the devices 102, 104, 110 in the system 100 and uploaded to the server 106 for storage in the database 108 in association with the patient. The demographic information may include, for example, the patient's height, weight, body mass index, age, ethnicity, residence information, or other information that may be utilized to classify the patient. In this regard, as demographic information associated with the patient changes (e.g., the patient gains or loses weight, ages, relocates, etc.), such updated demographic information may be uploaded or otherwise provided to the server 106 to update the patient's history stored in the database 108. The demographic information may also be stored in association with a timestamp or other temporal information to facilitate analysis and establishing correlations with other data to generate patient-specific models, as described below. Other clinically-relevant information may be obtained and utilized, either in addition to or alternatively to the demographic information. Such clinically-relevant information may include, for example, the patient's medical history, the patient's medication or drug history, the patient's hospitalization or other treatment information and records, or the like. For purposes of explanation the subject matter is primarily described herein in the context of utilizing demographic information, but it should be appreciated that clinically-relevant information may be similarly utilized in an equivalent manner.

In exemplary embodiments, the patient modeling process 200 continues by obtaining environmental and behavioral information associated with preceding operations of a sensing arrangement or infusion device (tasks 208, 210). In this regard, environmental and behavioral information concurrent to the measurement data, the delivery data, or potentially other data may be obtained and used to facilitate analysis of relationships between such data. The environmental information (e.g., temperature, humidity, and the like) may be received in any number of manners, such as, for example, via one or more environmental sensors integrated with the sensing arrangement 104, the infusion device 102, or the client device 110, via the network 114 from a remote resource using geolocation information associated with any one of the sensing arrangement 104, the infusion device 102, or the client device 110, or the like. Such environmental data may also be stored in association with a timestamp or other temporal information to facilitate analysis and establishing correlations with other data for generating patient-specific models, as described below.

Similarly, behavioral information may be received in any number of manners. For example, in one embodiment, the patient may manipulate a user input device associated with any one of the devices 102, 104, 110 to provide an indication of the type, duration, and/or other characteristics of activities that the patient is, has, or will be engaged in, which, in turn, may be uploaded from the respective device 102, 104, 110 to the server 106 via the network 114. In alternative embodiments, the behavioral information may be obtained from one or more sensing arrangements at the location of the patient, which may be either standalone sensing arrangements or integrated with any one of the devices 102, 104, 110. For example, an accelerometer, pedometer, or similar device capable of sensing or otherwise detecting motion by the patient may be worn by the patient or integrated with any one of the devices 102, 104, 110 carried on or by the patient to provide measurements of the motion of the patient, which, in turn, may be uploaded to the server 106 via the network 114. Similarly, a heart rate sensing arrangement or a similar sensing arrangement capable of sensing a physiological condition of the patient that is different from that measured by the sensing arrangement 104 to obtain measurements of a physiological condition correlative to activity by the patient. The behavioral data may also be stored in association with a timestamp or other temporal information to facilitate analysis and establishing correlations with other data for generating patient-specific models, as described below. The behavioral data may also include information such as the patient's usage of various sensor site locations (e.g., the sensor site location temporally associated with other pieces of data), the number or type of sensing arrangements being utilized by the patient, and potentially other aspects of the system 100 that are controlled, configured, or otherwise dictated by the patient.

In exemplary embodiments, the patient modeling process 200 also obtains historical values for the parameter of interest to be modeled for the patient (task 212). In this regard, the historical values for the parameter being modeled may also be uploaded to the server 106 via the network 114 by any one of the devices 102, 104, 110. For example, when the parameter of interest is a calibration factor for converting a measurement signal output by a sensing element of the sensing arrangement 104 to a corresponding measurement value, each time the sensing arrangement 104 is calibrated, the sensing arrangement 104 and/or the infusion device 102 may upload or otherwise transmit the resulting calibration factor to the server 106 for storage in the database 108 as part of the patient's history. In addition to the calibration factor values, the sensing arrangement 104 and/or the infusion device 102 may also upload the reference measurement values (e.g., reference blood glucose measurement values obtained using a fingerstick device, a portable blood glucose measurement device, or the like) and corresponding measurement signal values used to calculate the calibration factor, along with corresponding timestamps or other temporal information to facilitate analysis and establishing correlations.

In one or more embodiments, the server 106 stores or otherwise maintains, in the database 108, one or more files or entries associated with the patient that maintains an association between the patient's historical sensor glucose measurement data, the patient's historical bolus and meal data, the patient's historical reference blood glucose measurements, the patient's current and/or past demographic information, the historical context information associated with operation of the patient's sensing arrangement 104 and/or infusion device 102 (e.g., historical environmental data, behavioral data, and the like), and historical values for the parameter of interest, along with timestamps or other temporal information associated with the respective pieces of historical data. It should be noted that the patient modeling process 200 may support modeling any number of parameters of interest, such that the database 108 may store historical values for any number of parameters or variables utilized by the sensing arrangement 104 and/or the infusion device 102 to support respective operation thereof. In this regard, one parameter of interest may be modeled as a function of other parameters or variables in addition to the historical measurement, delivery, and contextual data, and those parameters or variables themselves may also be modeled as a function of the historical measurement, delivery, and contextual data.

Once a sufficient amount of historical data has been obtained by the server 106 and/or the database 108, the patient modeling process 200 continues with determining a patient-specific model for a parameter of interest based on the patient's historical data. In one embodiment, the patient modeling process 200 requires that data for at least a minimum threshold number of days (or hours) has been uploaded to continue. In other embodiments, additional thresholds may be utilized to determine when modeling can occur, such as, for example, a minimum number of historical values for the parameter of interest or the like.

Still referring to FIG. 2, to obtain a model for a parameter of interest, the patient modeling process 200 identifies or otherwise determines a subset of the historical data that is predictive of or correlative to the historical values for the parameter of interest for that individual patient and generating a patient-specific model of the parameter of interest for that patient using that predictive subset of variables (tasks 214, 216). In this regard, in exemplary embodiments, the server 106 utilizes machine learning to determine which combination of historical sensor measurement data, historical delivery data, demographics data, environmental data, behavioral data, and other historical parameter data are most strongly correlated to or predictive of the contemporaneous historical values for the parameter of interest, and then determines a corresponding equation for calculating the value of the parameter of interest based on that subset of input variables. Thus, the model is capable of characterizing or mapping a particular combination of one or more of the current (or recent) sensor glucose measurement data, delivery data, demographic information, environmental conditions, patient behavior, and the like to a current value for the parameter of interest, and vice versa. Since each patient's physiological response may vary from the rest of the population, the subset of input variables that are predictive of or correlative to the parameter of interest for that patient may vary from other users. Additionally, the relative weightings applied to the respective variables of that predictive subset may also vary from other patient's who may have common predictive subsets, based on differing correlations between a particular input variable and the historical values of the parameter of interest for that particular patient. It should be noted that any number of different machine learning techniques may be utilized by the server 106 to determine what input variables are predictive of the parameter of interest for the current patient of interest, such as, for example, artificial neural networks, genetic programming, support vector machines, Bayesian networks, probabilistic machine learning models, or other Bayesian techniques, fuzzy logic, heuristically derived combinations, or the like.

In one or more exemplary embodiments, only a subset of the historical data for the patient are used to develop the parameter model, with the remaining historical data being utilized by the patient modeling process 200 to test or otherwise validate the developed model (tasks 218, 220). For example, for the testing subset of the historical data, the server 106 applies the developed parameter model to the predictive variable values contemporaneous to or otherwise temporally associated with historical values for the modeled parameter, and then identifies or otherwise determines whether the model results are correlative to those historical values for the modeled parameter. In this regard, the server 106 compares the model-based parameter value calculated based on the predictive subset of historical data to the corresponding historical values for the modeled parameter and calculates or otherwise determines one or more metrics indicative of the performance of the model. For example, the server 106 may calculate or otherwise determine one or more correlation coefficient values associated with the developed model based on the differences between the model-based calculated parameter values and the corresponding historical values for the modeled parameter.

When the performance metrics associated with the developed model are greater than a threshold or otherwise satisfy applicable validation criteria, the patient modeling process 200 stores or otherwise maintains the parameter model in association with the patient for use in subsequently determining values for that parameter (task 222). For example, identification of the predictive variables for the patient for that particular parameter of interest along with the relative weightings or manner in which those predictive variables should be combined to calculate a value for the parameter of interest may be stored or otherwise maintained in the database 108 in association with a patient identifier assigned to or otherwise associated with the patient, the infusion device 102 and/or the sensing arrangement 104. As described in greater detail below, the validated model may then be utilized to determine a current value for the parameter of interest in real-time based on the current values of the predictive variables for that parameter in lieu of or in addition to other techniques. For example, a calibration factor model may be utilized to calculate or otherwise determine a current calibration factor value in real-time instead of relying on a new reference blood glucose measurement from a fingerstick device, a portable blood glucose measurement device, or the like. In some embodiments, the model could also be utilized to continually and dynamically vary the value of the parameter of interest as the values for the predictive variables change during operation. Additionally, the model may be utilized to augment or otherwise adjust a parameter value over time. For example, the calibration factor may be calculated or otherwise determined as a function of the modeled calibration factor value and a calibration factor value determined using a reference blood glucose measurement, where the relative weighting applied to the modeled calibration factor value increases and the relative weighting applied to the reference calibration factor value decreases as the amount of time that has elapsed since the reference blood glucose measurement was obtained increases.

In one or more embodiments, when the performance metrics associated with the developed model do not satisfy applicable validation criteria, the patient modeling process 200 discards the developed model and assigns or otherwise associates the patient with a broader population model (task 224). In this regard, the population model may be developed by performing various aspects of the patient modeling process 200 across a plurality of different patients. For example, in one embodiment, a patient may be assigned or otherwise associated with a particular group of patients having one or more characteristics in common based on the demographic information associated with that patient, with a parameter model for that patient group being determined based on the aggregated historical data for the different patients of the group. In one or more embodiments, the patient modeling process 200 assigns or otherwise associates the patient with a patient group parameter model upon initialization of the patient within the patient management system 100 prior to accumulating sufficient historical data for developing a patient-specific model.

It should be noted that in one or more embodiments, the patient modeling process 200 is performed repeatedly to dynamically update the model(s) substantially in real-time. For example, whenever new data becomes available from a particular source within a patient management system 100, the patient modeling process 200 may be repeated to dynamically update the parameter model as appropriate. That said, in other embodiments, once a sufficient amount of data has been obtained, or the parameter model has stabilized (e.g., no changes over a certain number of successive iterations of the patient modeling process 200), the parameter model may be persisted and the patient modeling process 200 may not be continually performed.

Figure 3:
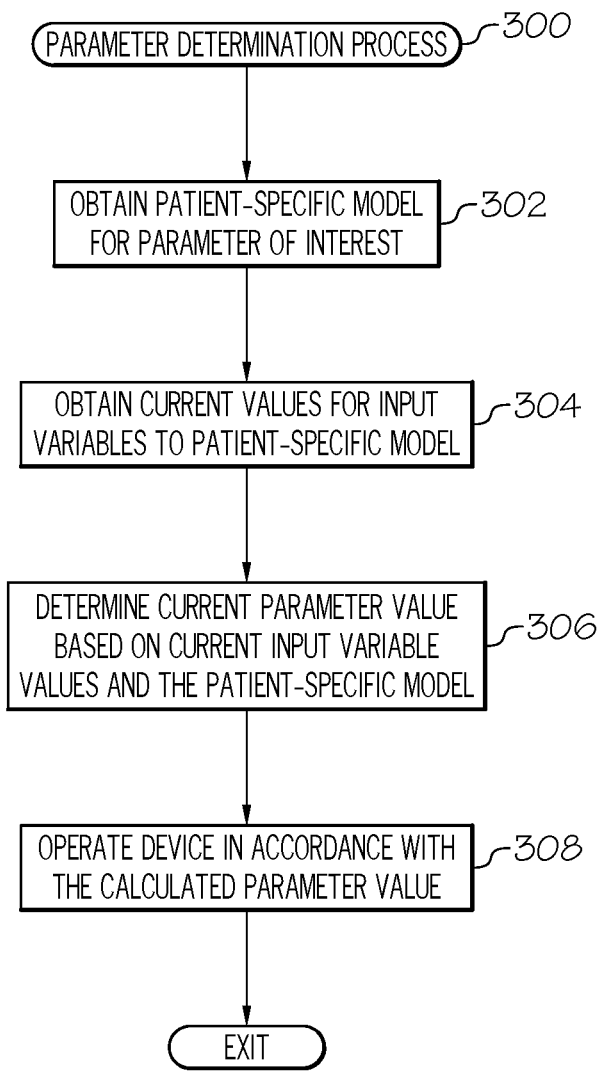
FIG. 3 is a flow diagram of an exemplary parameter determination process suitable for use with a parameter model generated by the patient modeling process of FIG. 2 in the patient management system of FIG. 1 in one or more exemplary embodiments.

FIG. 3 depicts an exemplary parameter determination process 300 suitable for implementation by one or more devices within a patient management system to calculate or otherwise determine a current value for a parameter in real-time using a patient-specific model for that parameter. The various tasks performed in connection with the parameter determination process 300 may be performed by hardware, firmware, software executed by processing circuitry, or any combination thereof. For illustrative purposes, the following description refers to elements mentioned above in connection with FIG. 1. In practice, portions of the parameter determination process 300 may be performed by different elements of the patient management system 100, such as, for example, the infusion device 102, the sensing arrangement 104, the server 106, the database 108, the client device 110, the client application 112, and/or the processing system 116. It should be appreciated that the parameter determination process 300 may include any number of additional or alternative tasks, the tasks need not be performed in the illustrated order and/or the tasks may be performed concurrently, and/or the parameter determination process 300 may be incorporated into a more comprehensive procedure or process having additional functionality not described in detail herein. Moreover, one or more of the tasks shown and described in the context of FIG. 3 could be omitted from a practical embodiment of the parameter determination process 300 as long as the intended overall functionality remains intact.

Generally, the parameter determination process 300 is performed whenever it is desirable to update the value for a parameter used to control or otherwise influence operation of a device within a patient management system 100, such as, for example, the sensing arrangement 104 or the infusion device 102. Depending on the embodiment, the parameter determination process 300 may be initiated automatically or manually, and could be performed continually, periodically, or asynchronously (e.g., whenever a value of a predictive variable changes). While the parameter determination process 300 is described herein primarily in the context of use with a patient-specific parameter model, it should be appreciated that the parameter determination process 300 may be implemented in an equivalent manner or population parameter models and the subject matter described herein is not necessarily limited to a patient-specific model.

The illustrated parameter determination process 300 begins by receiving or otherwise obtaining a patient-specific model for the parameter of interest (task 302). For example, the sensing arrangement 104 or the infusion device 102 may download or otherwise obtain, from the server 106 via the network 114, a patient-specific parameter model determined using the patient modeling process 200 (e.g., task 222) for a parameter utilized by that respective device 102, 104.

The parameter determination process 300 continues by obtaining the current values for the input variables identified by the obtained model as predictive or correlative to the parameter of interest for the patient and then calculating or otherwise determining a current value for the parameter based on the current input variable values using the obtained model (tasks 304, 306). In this regard, the obtained model indicates the input variables that are predictive of or correlative to the parameter of interest (e.g., task 214) along with the weightings or manner in which those input variables should be combined to arrive at a value for the parameter of interest (e.g., task 216). Thus, the sensing arrangement 104 or the infusion device 102 identifies the input variables for which values should be obtained, and then obtains the current, updated, or most recent values for those input variables from the appropriate source within the system 100. Once the current input variable values are obtained, the sensing arrangement 104 or the infusion device 102 calculates or otherwise determines a current value for the parameter of interest as a function of those current input variable values in the manner indicated by the parameter model. For example, in one embodiment, the sensing arrangement 104 or the infusion device 102 calculates the current value for the parameter of interest as a weighted sum of the current input variable values, where the weightings applied to the respective input variable values are indicated by parameter model and correspond to the relative strength of the correlation or predictiveness of the respective input variable to the parameter value.

In exemplary embodiments, the parameter determination process 300 continues by operating a respective device within the patient management system in accordance with the calculated parameter value or in a manner that is otherwise influenced by the calculated parameter value (task 308). In this regard, the calculated value for the parameter may influence, for example, the output of the sensing arrangement 104, the amount or rate of delivery of fluid by the infusion device 102, the type or manner of alerts or user notifications generated by a respective device 102, 104, 110, a GUI display presented on or by a respective device 102, 104, 110, or the like.

For example, referring to FIGS. 1-3, in accordance with one embodiment, the parameter determination process 300 may be utilized to determine an expected calibration factor for determining a calibrated current measurement of the glucose level in the body of the patient based on output signals from the sensing element of the sensing arrangement 104. For example, in one or more embodiments, a calibrated sensor glucose measurement (SG) is calculated using the following equation: SG=CF(isig−offset), where isig represents the measurement signal output by the sensing element of the sensing arrangement 104, offset represents an amount of offset associated with the measurement signal, and CF represents the calibration factor for converting the measurement signal into a corresponding glucose measurement value. In one embodiment, the measurement signal (isig) is an electrical current having a magnitude correlative to the patient's glucose level and the offset (offset) represents the amount of background current within the measurement signal that is substantially independent of the patient's glucose level. The patient modeling process 200 may be performed to obtain historical calibration factor values (e.g., task 212) for the patient determined based on reference blood glucose measurements along with other historical data contemporaneous or otherwise temporally related to those calibration factor values, and then determines an expected calibration factor model for the patient based on those historical calibration factor values and a subset of the historical data associated with the patient that are predictive of or correlative to the historical calibration factor values. For example, as described above, the model may indicate predictive variables for the calibration factor for the patient, such as, for example, the current sensor site location, the patient's current body mass index, the patient's gender, the current time of day, and the like.

Continuing the example, the parameter determination process 300 may be performed by the sensing arrangement 104 to obtain the patient's calibration factor model from the server 106 and then calculate or otherwise determine the calibration factor value to be utilized in determining a calibrated sensor glucose measurement value as a function of the current sensor site location, the patient's current body mass index, the patient's gender, the current time of day, and the like in accordance with the relative weighting or manner of combination dictated by the patient's calibration factor model. Thus, rather than requiring a new fingerstick measurement, the sensing arrangement 104 may periodically update the calibration factor value using the calibration factor model, and then use the calculated calibration factor value to calculate a calibrated sensor glucose measurement value (SG) based on measurement signals from its sensing element, which are then transmitted, output, or otherwise provided to another device 102, 110. In this manner, the calibration factor model may influence the output provided by the sensing arrangement 104, which, in turn, may influence operation of the infusion device 102 (e.g., by influencing delivery of fluid determined based on the current sensor glucose measurement value, suspending or resuming delivery based on the current sensor glucose measurement value, or the like) or influence GUI displays, alerts, or other user notifications generated by another device 102, 110 based on the current sensor glucose measurement value. That said, in other embodiments, the parameter determination process 300 may be performed by the infusion device 102, the remote device 106, or the client device 110 to calculate an expected calibration factor value to be utilized to convert measurement signals received from the sensing arrangement 104 into calibrated sensor glucose measurement values at the respective device 102, 106, 110.

In one embodiment, the expected calibration factor model is used in conjunction with determining a calibration factor using a fingerstick measurement or other reference glucose value. For example, when a sensing arrangement 104 is initially inserted at a sensor site location, transients may undesirably influence the calibration factor value determined using a reference measurement value. Thus, the expected calibration factor may be dynamically calculated and used to normalize or otherwise adjust the calibration factor value determined using a reference measurement value to improve the accuracy of the calibration factor value utilized by the sensing arrangement 104 and/or the infusion device 102. For example, the sensing arrangement 104 may dynamically calculate an updated calibration factor value as a weighted sum of the initial calibration factor value determined based on a reference measurement value and the expected calibration factor value based on the current values of the predictive variables for the patient's calibration factor, with the relative weightings varying over time in a manner that accounts for the behavior of the sensing arrangement 104 after insertion.

As another example, the parameter determination process 300 may be utilized to determine an expected offset associated with the measurement signal for use in determining a calibrated current measurement of the glucose level in the body of the patient based on output signals from the sensing element of the sensing arrangement 104. In this regard, the patient modeling process 200 obtains historical offset values (e.g., task 212) for the patient determined based on reference blood glucose measurements along with other historical data contemporaneous or otherwise temporally related to those calibration factor values, and then determines an expected calibration factor model for the patient based on those historical offset values and a subset of the historical data associated with the patient that are predictive of or correlative to the historical offset values. For example, the model may indicate predictive variables for the offset value for the patient, such as, for example, the patient's current insulin sensitivity factor, the current sensor site location, and the like.

In a similar manner as described above, the parameter determination process 300 may be performed by the sensing arrangement 104 to obtain the patient's measurement signal offset model from the server 106 and then calculate or otherwise determine the offset value to be utilized in determining a calibrated sensor glucose measurement value as a function of the current sensor site location, the patient's current insulin sensitivity factor, and the like in accordance with the relative weighting or manner of combination dictated by the patient's measurement signal offset model. In one embodiment, the current measurement signal offset value calculated using the patient's predictive variables according to the patient's measurement signal offset model influences calibration factor values determined based on a reference measurement, for example, by applying the calculated offset to the measurement signal(s) utilized in the calibration factor calculation. The calculated measurement signal offset value may also be utilized in conjunction with a calculated calibration factor value from the patient's expected calibration factor model to determine calibrated sensor glucose measurements values.

In one or more embodiments, the parameter determination process 300 is utilized to determine an time-dependent expected offset associated with the measurement signal for use in determining a calibrated sensor glucose measurement. In this regard, the patient modeling process 200 determines a time-dependent expected offset model for the patient based on those historical offset values and an amount of time elapsed after sensor site insertion and potentially other historical data associated with the patient that are predictive of or correlative to the historical behavior of the historical offset values relative to the time of sensor site insertion. Thus, the parameter determination process 300 may be performed by the sensing arrangement 104 to obtain the patient's measurement signal offset model from the server 106 and then dynamically calculate or otherwise determine the offset value to be utilized in determining a calibrated sensor glucose measurement value as a function of the amount of time elapsed since insertion at the current sensor site location, the particular sensor site location, and potentially other predictive variables. As a result, the relationship between the calibrated sensor measurement value output by the sensing arrangement 104 and the measurement signals output by the sensing element of the sensing arrangement 104 may dynamically vary in a manner that accounts for the behavior of the sensing element over time after being inserted at the particular sensor site location.

In other embodiments, the processes 200, 300 are utilized to generate GUI displays or user notifications for the patient. For example, in one embodiment, the patient modeling process 200 may be performed to generate a model of the sensor accuracy and/or sensor stability as a function of an amount of time elapsed after sensor site insertion, the time since last calibration, the current sensor site location, behavioral patterns, and other predictive variables of sensor accuracy for the particular patient. Thereafter, upon insertion of the sensing arrangement 104 at a particular site location, the parameter determination process 300 may be performed by any one of the devices 102, 104, 106, 110 in the system 100 to determine an amount of time after the sensor site insertion time for which the sensor accuracy or stability is at its maximum value using the model, the current sensor site location, and the current values for the other predictive variables of sensor accuracy or stability for the particular patient. In this regard, after identifying an amount of elapsed time that yields the best sensor accuracy or stability, the respective device 102, 104, 106, 110 may calculate or otherwise determine a corresponding time of day when the patient should calibrate the sensing arrangement 104 (e.g., using a fingerstick or other reference measurement) and generate or otherwise provide indication of that optimal time for calibration. For example, the infusion device 102 or the client device 110 may generate or otherwise provide a graphical representation of the optimal calibration time on its respective display device. In one embodiment, the infusion device 102 or the client device 110 monitors the current time and automatically generates or otherwise provides a user notification or alert when the current time corresponds to the optimal calibration time determined using the model. In some embodiments, the optimal calibration time may be dynamically updated in response to changes in one or more predictive variable values.

In one or more embodiments, historical values for sensor accuracy are calculated retrospectively by quantifying the performance or accuracy of previous calibrations based on the relationship between historical reference blood glucose measurement values and corresponding calibration factors. Modeling the sensor accuracy as a function of a subset of predictive variables, the parameter determination process 300 may be performed to estimate or otherwise determine a current sensor accuracy value using the model and provide a corresponding indication to replace the sensing arrangement when the current accuracy value falls below a replacement threshold. As another example, historical values for sensor sensitivity may be calculated based on changes in the historical calibration factor values over time. In this regard, increasing calibration factor values are indicative of decreasing sensitivity. By modeling the sensitivity values as a function of the characteristic impedance, time since insertion, and the like, the parameter determination process 300 may be performed to estimate or otherwise determine a current sensor sensitivity value using the model and provide a corresponding indication to replace the sensing arrangement when the current sensitivity value falls below a replacement threshold.

As described above, by correlating predictive variables characterizing the operational context associated with the sensor calibration, such as the time of day, location, patient behavior or activity, or the like, with the resulting sensor accuracy, the best operational context for calibrations may be identified for a particular patient. Additionally, the sensor accuracy model may be utilized to identify the frequency or rate at which a particular patient should calibrate his or her sensing arrangement. For example, an individual patient's sensor accuracy model may indicate a relatively strong correlation between the sensor accuracy and the amount of time that has elapsed since the most recent calibration, such that that patient should recalibrate the sensing arrangement every 6 hours to achieve a desired likelihood of maintaining a sensor accuracy above a recalibration threshold value. Conversely, other patients may exhibit a lesser correlation between sensor accuracy and elapsed time since sensor calibration, and thus, can recalibrate the sensing arrangement at a lower frequency. Accordingly, the sensing arrangement 104 or the client device 110 may utilize the sensor accuracy model to calculate or otherwise determine a current sensor accuracy value and provide a corresponding indication to the patient recommending recalibration when the calculated value is less than the recalibration threshold value. Thus, the sensor accuracy model may be utilized to not only identify optimal times of day or other optimal operating contexts for calibrating the sensing arrangement, but also provide notifications or alerts on a periodic basis alerting the patient of a potential need to recalibrate in a manner that is unique to that particular patient.

As another example, in one embodiment, the patient modeling process 200 may be performed to generate a model of the remaining usage life of the sensing arrangement 104 (or the sensing element associated therewith) as a function of current sensor glucose measurement values, the current sensor site location, the current environmental conditions and/or other predictive variables of sensor life for the particular patient. In this regard, the parameter determination process 300 may be periodically performed by any one of the devices 102, 104, 106, 110 in the system 100 to determine an estimated amount of useful life remaining for the sensing arrangement 104 using the developed model of sensor usage life for the particular patient. The respective device 102, 104, 106, 110 may generate or otherwise provide a graphical representation of the estimated remaining usage life to the patient.

In one embodiment, in addition to the measurement signal, the sensing arrangement 104 obtains or otherwise provides a characteristic impedance associated with the sensing element and/or the sensing arrangement 104. In such embodiments, the patient modeling process 200 may obtain historical values for the characteristic impedance and corresponding metrics for historical sensor performance (e.g., accuracy, sensitivity, or the like) and usage life and a model of the remaining usage life of the sensing arrangement 104 as a function of the characteristic impedance. The remaining usage life model may account for historical patterns in the characteristic impedance when sensor performance decreases or the sensor is terminated or replaced. In other embodiments, the remaining usage life model may account for other patterns in the patient's historical data contemporaneous to sensor performance decreases or sensor termination or replacement, such as, for example, historical calibration factor value patterns, measurement signal patterns, or the like. Additionally, the remaining usage life model may account for environmental conditions, patient demographics, sensor site locations or site rotation patterns, or other factors that are predictive of the remaining usage life for that particular patient.

In another embodiment, the remaining usage life model is utilized to calculate or otherwise determine a value for an adjustment factor based on remaining usage life predictive variables for the patient, which, in turn, is utilized to influence or adjust the calculation of the remaining usage life based on the characteristic impedance. For example, in one embodiment, a linear equation may be utilized to extrapolate the characteristic impedance from the current value to a replacement value based on the gradient of the characteristic impedance, with the remaining usage life corresponding to the temporal difference between the current time and the future time associated with the extrapolated replacement value. In one embodiment, the remaining usage life for when the sensor should be replaced is calculated using the equation $$\frac{EIS_{ref} - EIS_{current} - EIS_r}{G},$$

where $EIS_{ref}$ represents a preceding value for the characteristic impedance, $EIS_{current}$ represents a current value for the characteristic impedance, $EIS_r$ represents a replacement value for the characteristic impedance, and G represents the gradient of the characteristic impedance between the preceding value and the current value calculated by $$\frac{EIS_{current} - EIS_{ref}}{t},$$

where t is the duration of time between the current and preceding values. In this regard, the adjustment factor determined using the remaining usage life model may be utilized to adjust any one of the terms in the equations for the remaining usage life and the gradient, either individually or collectively, in a manner that reduces the difference between the calculated remaining usage life and the actual remaining usage life. Expressed another way, the model may be utilized to tune or adjust the linear equation to improve the estimate of the sensor's remaining usage life using current values for predictive variables for the particular patient that define the current operational context for the sensing arrangement 104.

In other embodiments, the processes 200, 300 are utilized to generate models that may be utilized to calculate control parameters or settings variables that dictate operations of the infusion device 102 or the sensing arrangement 104. For example, in one embodiment, the patient modeling process 200 is performed to generate a model of tissue properties (or tissue resistance) associated with the sensing arrangement 104 and/or the infusion device 102 as a function of the current sensor site location, the current infusion site location, the current body mass index for the patient, the current characteristic impedance and/or other predictive variables of sensor life for the particular patient. The parameter determination process 300 may then be performed by the respective device 102, 104 to calculate a current value for the tissue property based on current values for the predictive variables indicated by the patient's tissue property model, and then adjusting or altering operation of the respective device 102, 104 based on the calculated tissue property value. For example, the sensing arrangement 104 may utilize the calculated tissue property value to identify the current sensor site location and/or adjust one or more parameters, such as the calibration factor, the offset, or the like, to obtain sensor glucose measurement value that accounts for the tissue property at the current sensor site location. In other embodiments, the infusion device 102 may utilize the calculated tissue property value to adjust or otherwise alter control parameters that influence the sensitivity or responsiveness of an autonomous control scheme implemented by the infusion device 102 improve regulation of the patient's glucose level in a manner that accounts for the tissue property at the current sensor site location.

In yet other embodiments, any one of the devices 102, 104, 106, 110 in the system 100 may utilize the calculated tissue property value to generate or otherwise provide GUI displays or other notifications for the patient. For example, based on the calculated tissue property value, the sensing arrangement 104 and/or the client device 110 may generate or otherwise provide an alert that notifies the patient to rotate the sensing arrangement from the current sensing arrangement 104. In other embodiments, the calculated tissue property value(s) may be utilized to determine recommended sensor site locations or recommended sensor site rotation patterns and provide a corresponding guidance GUI display that informs the patient of the manner in which site locations could be utilized to improve performance. The calculated tissue property value(s) may also be utilized to identify the current sensor site location and adjust or otherwise modify control parameters to optimize performance for the current sensor site location.

It should be noted that the above examples are provided primarily for purposes of illustration and are not intended to be limiting. In practice, the patient modeling process 200 may be performed to generate a model for calculating any parameter of interest based on any number or type of predictive variables identified based on historical values for the parameter of interest and those predictive variables. Likewise, the parameter determination process 300 may be performed to calculate an expected or likely value for a parameter of interest based on current values for the predictive variables using the model. In other words, the subject matter described herein is not intended to be limited to any particular subset of predictive input variables for the model or any particular parameter of interest to be calculated therefrom. Additionally, it should be appreciated that the processes 200, 300 may be implemented in concert or concurrently to support modeling of any number of parameters of interest and calculating current values for such modeled parameters concurrently.

It should also be noted that not only may the above processes 200, 300 improve operations of the infusion device 102 and/or the sensing arrangement 104 in a manner that improves the glucose regulation achieved by the system 100, the processes 200, 300 may also improve the user experience by decreasing the number or frequency of affirmative actions that need to be performed by the patient to effectuate improved glucose regulation or otherwise maintaining the patient apprised of the current operations of the devices 102, 104 and various means for improving performance. For example, the processes 200, 300 may be utilized to model the patient's calibration factors, insulin sensitivity factors, or the like and allow those patient-specific factors to be calculated, estimated, or otherwise determined in a manner that obviates the need for the patient to manually obtain calibration measurements, manually input various values, or the like. Additionally, when the processes 200, 300 is utilized to model remaining usage life of the sensing arrangement 104, the patient may be apprised of the remaining usage life or the time of when the patient will need to replace, rotate, or otherwise modify the sensing arrangement 104 in advance of the need arising, thereby reducing frustration and inconvenience as well as facilitating an improved understanding of the current status or functionality of the sensing arrangement 104. Similarly, providing guidance or recommendations for sensor site rotations based on calculated values from patient-specific models reduces the burden on the patient of determining when or how to rotate sensor sites and improves the patient's understanding and control of his or her sensor usage.

Figure 4:
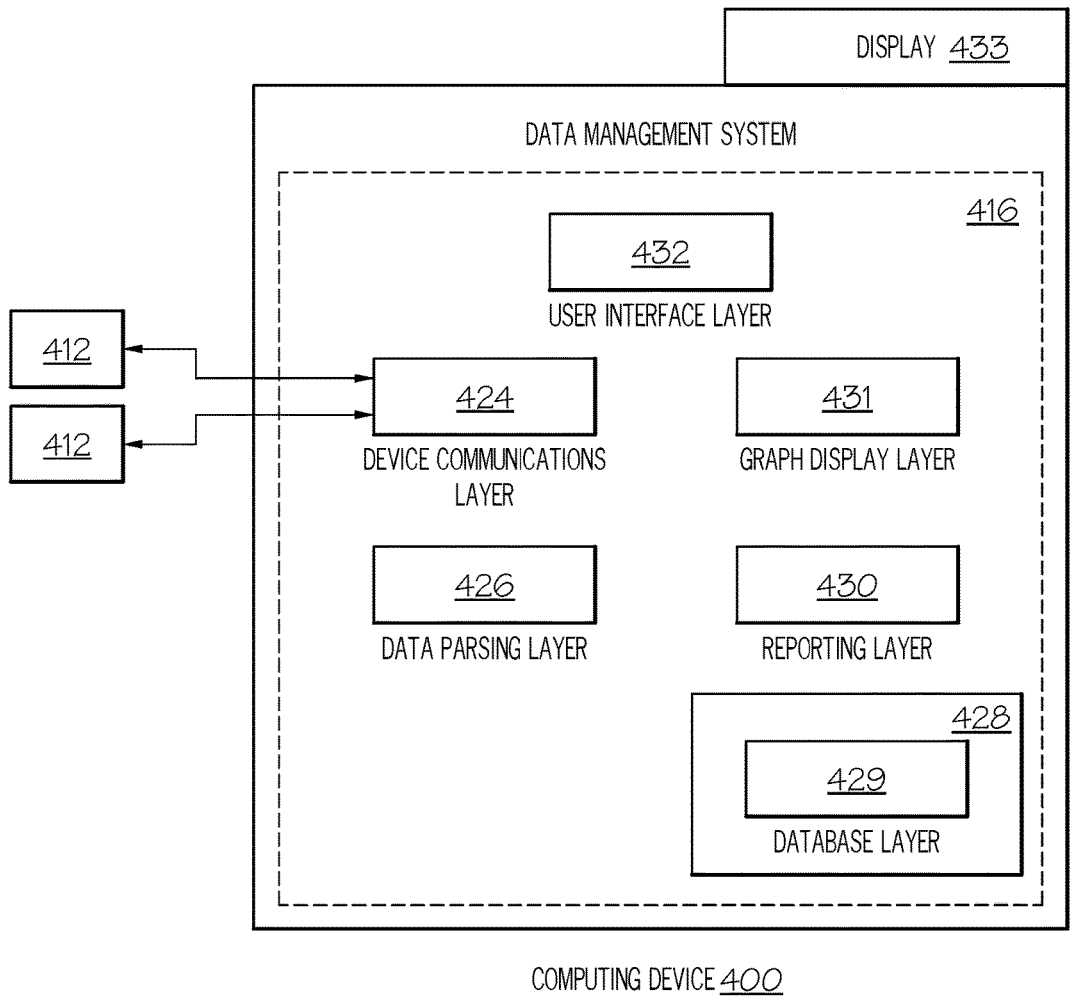
FIG. 4 depicts an embodiment of a computing device for a diabetes data management system in accordance with one or more embodiments.

FIG. 4 illustrates a computing device 400 suitable for use in a diabetes data management system in conjunction with the processes 200, 300 of FIGS. 2-3 described above. The diabetes data management system (DDMS) may be referred to as the Medtronic MiniMed CARELINK™ system or as a medical data management system (MDMS) in some embodiments. The DDMS may be housed on a server (e.g., server 106) or a plurality of servers which a user or a health care professional may access via a communications network via the Internet or the World Wide Web. Some models of the DDMS, which is described as an MDMS, are described in U.S. Patent Application Publication Nos. 2006/0031094 and 2013/0338630, which is herein incorporated by reference in their entirety.

While description of embodiments are made in regard to monitoring medical or biological conditions for subjects having diabetes, the systems and processes herein are applicable to monitoring medical or biological conditions for cardiac subjects, cancer subjects, HIV subjects, subjects with other disease, infection, or controllable conditions, or various combinations thereof.

In various embodiments, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 400. The computing device 400 may be coupled to a display 433. In some embodiments, the computing device 400 may be in a physical device separate from the display (such as in a personal computer, a mini-computer, etc.) In some embodiments, the computing device 400 may be in a single physical enclosure or device with the display 433 such as a laptop where the display 433 is integrated into the computing device. In various embodiments, the computing device 400 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/glucose sensor having a display. The computing device may also be an insulin pump coupled to a display, a glucose meter coupled to a display, or a glucose sensor coupled to a display. The computing device 400 may also be a server located on the Internet that is accessible via a browser installed on a laptop computer, desktop computer, a network computer, or a PDA. The computing device 400 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 402.11 protocols.

In the embodiment shown in FIG. 4, the data management system 416 comprises a group of interrelated software modules or layers that specialize in different tasks. The system software includes a device communication layer 424, a data parsing layer 426, a database layer 428, database storage devices 429, a reporting layer 430, a graph display layer 431, and a user interface layer 432. The diabetes data management system may communicate with a plurality of subject support devices 412, two of which are illustrated in FIG. 4. Although the different reference numerals refer to a number of layers, (e.g., a device communication layer, a data parsing layer, a database layer), each layer may include a single software module or a plurality of software modules. For example, the device communications layer 424 may include a number of interacting software modules, libraries, etc. In some embodiments, the data management system 416 may be installed onto a non-volatile storage area (memory such as flash memory, hard disk, removable hard, DVD-RW, CD-RW) of the computing device 400. If the data management system 416 is selected or initiated, the system 416 may be loaded into a volatile storage (memory such as DRAM, SRAM, RAM, DDRAM) for execution.

The device communication layer 424 is responsible for interfacing with at least one, and, in further embodiments, to a plurality of different types of subject support devices 412, such as, for example, blood glucose meters, glucose sensors/ monitors, or an infusion pump. In one embodiment, the device communication layer 424 may be configured to communicate with a single type of subject support device 412. However, in more comprehensive embodiments, the device communication layer 424 is configured to communicate with multiple different types of subject support devices 412, such as devices made from multiple different manufacturers, multiple different models from a particular manufacturer and/or multiple different devices that provide different functions (such as infusion functions, sensing functions, metering functions, communication functions, user interface functions, or combinations thereof). By providing an ability to interface with multiple different types of subject support devices 412, the diabetes data management system 416 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 424 allows the DDMS 416 to receive information from and transmit information to or from each subject support device 412 in the system 416. Depending upon the embodiment and context of use, the type of information that may be communicated between the system 416 and device 412 may include, but is not limited to, data, programs, updated software, education materials, warning messages, notifications, device settings, therapy parameters, or the like. The device communication layer 424 may include suitable routines for detecting the type of subject support device 412 in communication with the system 416 and implementing appropriate communication protocols for that type of device 412. Alternatively or in addition, the subject support device 412 may communicate information in packets or other data arrangements, where the communication includes a preamble or other portion that includes device identification information for identifying the type of the subject support device. Alternatively, or in addition, the subject support device 412 may include suitable user-operable interfaces for allowing a user to enter information, such as by selecting an optional icon or text or other device identifier, that corresponds to the type of subject support device used by that user. Such information may be communicated to the system 416, through a network connection. In yet further embodiments, the system 416 may detect the type of subject support device 412 it is communicating with and then may send a message requiring the user to verify that the system 416 properly detected the type of subject support device being used by the user. For systems 416 that are capable of communicating with multiple different types of subject support devices 412, the device communication layer 424 may be capable of implementing multiple different communication protocols and selects a protocol that is appropriate for the detected type of subject support device.

The data-parsing layer 426 is responsible for validating the integrity of device data received and for inputting it correctly into a database 429. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 416 may compare received identification information with pre-stored information to evaluate whether the received information is from a valid source.

The database layer 428 may include a centralized database repository that is responsible for warehousing and archiving stored data in an organized format for later access, and retrieval. The database layer 428 operates with one or more data storage device(s) 429 suitable for storing and providing access to data in the manner described herein. Such data storage device(s) 429 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. Information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 416 or other entities, for analyzing group data or other forms of conglomerate data.

Embodiments of the database layer 428 and other components of the system 416 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 428 may be configured to limit access of each user to types of information pre-authorized for that user. For example, a subject may be allowed access to his or her individual medical information (with individual identifiers) stored by the database layer 428, but not allowed access to other subject's individual medical information (with individual identifiers). Similarly, a subject's authorized healthcare provider or payor entity may be provided access to some or all of the subject's individual medical information (with individual identifiers) stored by the database layer 428, but not allowed access to another individual's personal information. Also, an operator or administrator-user (on a separate computer communicating with the computing device 400) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 428 in the data storage devices 429.

In embodiments of the subject matter described herein, the database layer 428 may store patient-specific parameter models, population group parameter models, and corresponding historical data for various potential input variables and parameters of interest from which such models may be derived. In the database layer 428, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 429 in the database layer. The preference profiles may include various threshold values, monitoring period values, prioritization criteria, filtering criteria, and/or other user-specific values for parameters utilized to generate a snapshot GUI display on the display 433 or a support device 412 in a personalized or patient-specific manner. Additionally, data or information defining the parameter models associated with a particular individual may also be stored in a record, a file, or a memory location associated with that patient in the data storage device(s) 429 in the database layer.

The DDMS 416 may measure, analyze, and track either blood glucose (BG) or sensor glucose (SG) readings for a user. In exemplary embodiments, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 430 may include a report wizard program that pulls data from selected locations in the database 429 and generates report information from the desired parameters of interest. The reporting layer 430 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar. In exemplary embodiments described herein, the reporting layer 430 also facilitates generation of a snapshot report including a snapshot GUI display.

In some embodiments, the database layer 428 may calculate values for various medical information that is to be displayed on the reports generated by the report or reporting layer 430. For example, the database layer 428, may calculate average blood glucose or sensor glucose readings for specified timeframes. In some embodiments, the reporting layer 430 may calculate values for medical or physical information that is to be displayed on the reports. For example, a user may select parameters which are then utilized by the reporting layer 430 to generate medical information values corresponding to the selected parameters. In other embodiments, the user may select a parameter profile that previously existed in the database layer 428.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs. In this manner, users may import data from the system 416 into further reporting tools familiar to the user. The reporting layer 430 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 430 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 416 may allow a user generating a report to designate the report as non-printable and/or non-transferable, whereby the system 416 will provide the report in a form that inhibits printing and/or electronic transfer.

The reporting layer 430 may transfer selected reports to the graph display layer 431. The graph display layer 431 receives information regarding the selected reports and converts the data into a format that can be displayed or shown on a display 433.

In various embodiments, the reporting layer 430 may store a number of the user's parameters. Illustratively, the reporting layer 430 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 432 supports interactions with the end user, for example, for user login and data access, software navigation, data input, user selection of desired report types and the display of selected information. Users may also input parameters to be utilized in the selected reports via the user interface layer 432. Examples of users include but are not limited to: healthcare providers, healthcare payer entities, system operators or administrators, researchers, business entities, healthcare institutions and organizations, or the like, depending upon the service being provided by the system and depending upon the embodiment. More comprehensive embodiments are capable of interacting with some or all of the above-noted types of users, wherein different types of users have access to different services or data or different levels of services or data.

In an example embodiment, the user interface layer 432 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 416, depending upon the embodiment of use.

In another example embodiment, where the DDMS 416 is located on one computing device 400, the user interface layer 432 provides a number of menus to the user to navigate through the DDMS. These menus may be created utilizing any menu format, including but not limited to HTML, XML, or Active Server pages. A user may access the DDMS 416 to perform one or more of a variety of tasks, such as accessing general information made available on a website to all subjects or groups of subjects. The user interface layer 432 of the DDMS 416 may allow a user to access specific information or to generate reports regarding that subject's medical condition or that subject's medical device(s) 412, to transfer data or other information from that subject's support device(s) 412 to the system 416, to transfer data, programs, program updates or other information from the system 416 to the subject's support device(s) 412, to manually enter information into the system 416, to engage in a remote consultation exchange with a healthcare provider, or to modify the custom settings in a subject's supported device and/or in a subject's DDMS/MDMS data file.

The system 416 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 416 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 416, based on the type of user and/or the identity of the user.

Upon entering successful verification of the user's identification information and password, the user may be provided access to secure, personalized information stored on the DDMS 416. For example, the user may be provided access to a secure, personalized location in the DDMS 416 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 412 to the system 416, manually enter additional data into the system 416, modify the subject's custom settings, and/or view and print reports. Reports may include data specific to the subject's condition, including but not limited to, data obtained from the subject's subject support device(s) 412, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 429) employed by the database layer 428.

The user may select an option to transfer (send) device data to the medical data management system 416. If the system 416 receives a user's request to transfer device data to the system, the system 416 may provide the user with step-by-step instructions on how to transfer data from the subject's supported device(s) 412. For example, the DDMS 416 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 412 used by the subject. The system 416 employs that information to select the stored instruction set(s) associated with the particular subject's support device(s) 412 for display to the user.

Other activities or resources available to the user on the system 416 may include an option for manually entering information to the DDMS/MDMS 416. For example, from the user's personalized menu or location, the user may select an option to manually enter additional information into the system 416.

Further optional activities or resources may be available to the user on the DDMS 416. For example, from the user's personalized menu, the user may select an option to receive data, software, software updates, treatment recommendations or other information from the system 416 on the subject's support device(s) 412. If the system 416 receives a request from a user to receive data, software, software updates, treatment recommendations or other information, the system 416 may provide the user with a list or other arrangement of multiple selectable icons or other indicia representing available data, software, software updates or other information available to the user.

Yet further optional activities or resources may be available to the user on the medical data management system 416 including, for example, an option for the user to customize or otherwise further personalize the user's personalized location or menu. In particular, from the user's personalized location, the user may select an option to customize parameters for the user. In addition, the user may create profiles of customizable parameters. When the system 416 receives such a request from a user, the system 416 may provide the user with a list or other arrangement of multiple selectable icons or other indicia representing parameters that may be modified to accommodate the user's preferences. When a user selects one or more of the icons or other indicia, the system 416 may receive the user's request and makes the requested modification.

Figure 5:
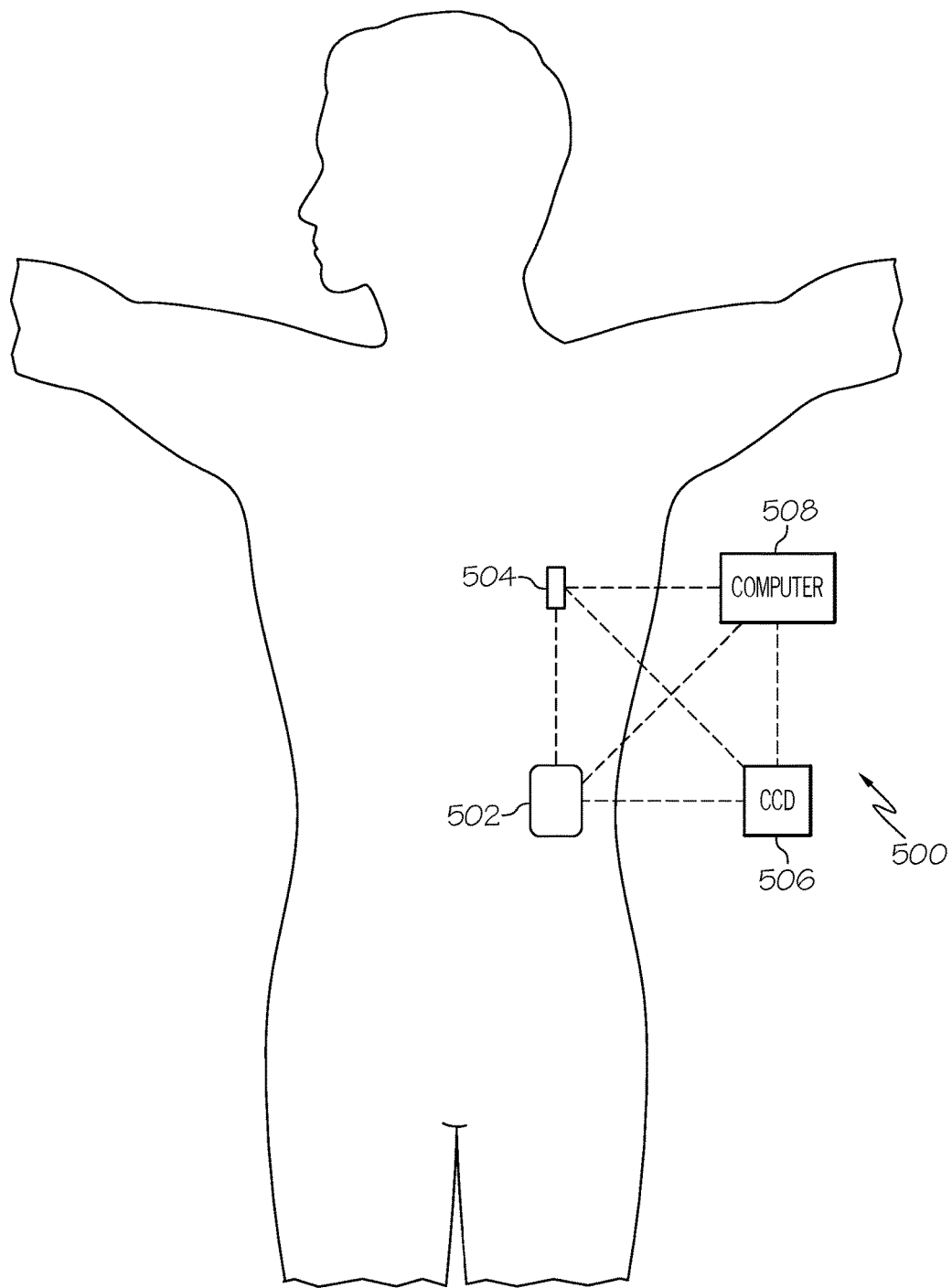
FIG. 5 depicts an exemplary embodiment of an infusion system.

FIG. 5 depicts one exemplary embodiment of an infusion system 500 that includes, without limitation, a fluid infusion device (or infusion pump) 502 (e.g., infusion device 102), a sensing arrangement 504 (e.g., sensing arrangement 104), a command control device (CCD) 506, and a computer 508, which could be realized as any one of the computing devices 106, 110, 400 described above. The components of an infusion system 500 may be realized using different platforms, designs, and configurations, and the embodiment shown in FIG. 5 is not exhaustive or limiting. In practice, the infusion device 502 and the sensing arrangement 504 are secured at desired locations on the body of a user (or patient), as illustrated in FIG. 5. In this regard, the locations at which the infusion device 502 and the sensing arrangement 504 are secured to the body of the user in FIG. 5 are provided only as a representative, non-limiting, example. The elements of the infusion system 500 may be similar to those described in U.S. Pat. No. 8,674,288, the subject matter of which is hereby incorporated by reference in its entirety.

In the illustrated embodiment of FIG. 5, the infusion device 502 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 504 generally represents the components of the infusion system 500 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 504 may include electronics and enzymes reactive to a biological or physiological condition of the user, such as a blood glucose level, or the like, and provide data indicative of the blood glucose level to the infusion device 502, the CCD 506 and/or the computer 508. For example, the infusion device 502, the CCD 506 and/or the computer 508 may include a display for presenting information or data to the user based on the sensor data received from the sensing arrangement 504, such as, for example, a current glucose level of the user, a graph or chart of the user's glucose level versus time, device status indicators, alert messages, or the like. In other embodiments, the infusion device 502, the CCD 506 and/or the computer 508 may include electronics and software that are configured to analyze sensor data and operate the infusion device 502 to deliver fluid to the body of the user based on the sensor data and/or preprogrammed delivery routines. Thus, in exemplary embodiments, one or more of the infusion device 502, the sensing arrangement 504, the CCD 506, and/or the computer 508 includes a transmitter, a receiver, and/or other transceiver electronics that allow for communication with other components of the infusion system 500, so that the sensing arrangement 504 may transmit sensor data or monitor data to one or more of the infusion device 502, the CCD 506 and/or the computer 508.

Still referring to FIG. 5, in various embodiments, the sensing arrangement 504 may be secured to the body of the user or embedded in the body of the user at a location that is remote from the location at which the infusion device 502 is secured to the body of the user. In various other embodiments, the sensing arrangement 504 may be incorporated within the infusion device 502. In other embodiments, the sensing arrangement 504 may be separate and apart from the infusion device 502, and may be, for example, part of the CCD 506. In such embodiments, the sensing arrangement 504 may be configured to receive a biological sample, analyte, or the like, to measure a condition of the user.

In various embodiments, the CCD 506 and/or the computer 508 may include electronics and other components configured to perform processing, delivery routine storage, and to control the infusion device 502 in a manner that is influenced by sensor data measured by and/or received from the sensing arrangement 504. By including control functions in the CCD 506 and/or the computer 508, the infusion device 502 may be made with more simplified electronics. However, in other embodiments, the infusion device 502 may include all control functions, and may operate without the CCD 506 and/or the computer 508. In various embodiments, the CCD 506 may be a portable electronic device. In addition, in various embodiments, the infusion device 502 and/or the sensing arrangement 504 may be configured to transmit data to the CCD 506 and/or the computer 508 for display or processing of the data by the CCD 506 and/or the computer 508.

In some embodiments, the CCD 506 and/or the computer 508 may provide information to the user that facilitates the user's subsequent use of the infusion device 502. For example, the CCD 506 may provide information to the user to allow the user to determine the rate or dose of medication to be administered into the user's body. In other embodiments, the CCD 506 may provide information to the infusion device 502 to autonomously control the rate or dose of medication administered into the body of the user. In some embodiments, the sensing arrangement 504 may be integrated into the CCD 506. Such embodiments may allow the user to monitor a condition by providing, for example, a sample of his or her blood to the sensing arrangement 504 to assess his or her condition. In some embodiments, the sensing arrangement 504 and the CCD 506 may be used for determining glucose levels in the blood and/or body fluids of the user without the use of, or necessity of, a wire or cable connection between the infusion device 502 and the sensing arrangement 504 and/or the CCD 506.

In one or more exemplary embodiments, the sensing arrangement 504 and/or the infusion device 502 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153, all of which are incorporated herein by reference in their entirety. In such embodiments, the sensing arrangement 504 is configured to sense or measure a condition of the user, such as, blood glucose level or the like. The infusion device 502 is configured to deliver fluid in response to the condition sensed by the sensing arrangement 504. In turn, the sensing arrangement 504 continues to sense or otherwise quantify a current condition of the user, thereby allowing the infusion device 502 to deliver fluid continuously in response to the condition currently (or most recently) sensed by the sensing arrangement 504 indefinitely. In some embodiments, the sensing arrangement 504 and/or the infusion device 502 may be configured to utilize the closed-loop system only for a portion of the day, for example only when the user is asleep or awake.

Figure 6:
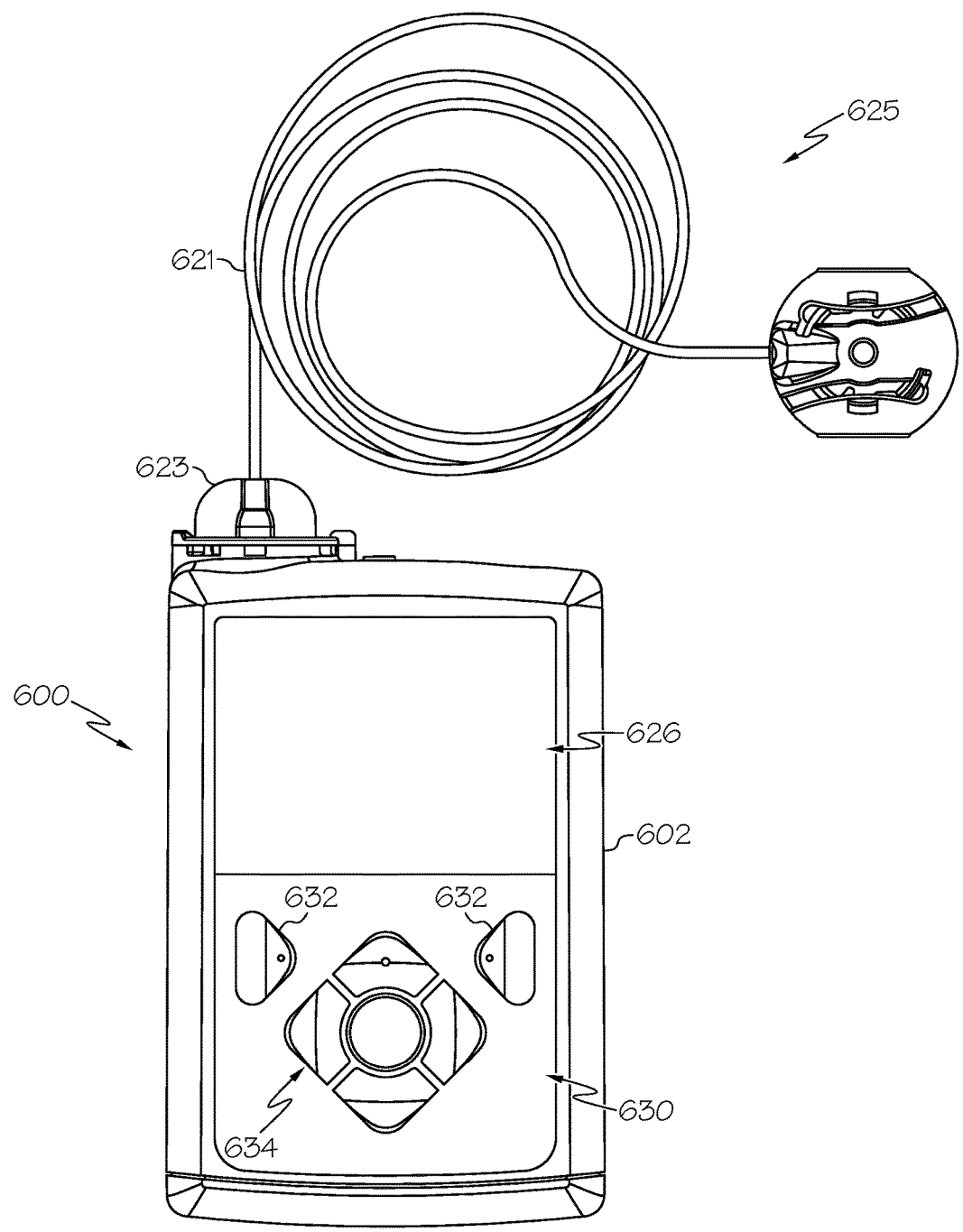
FIG. 6 depicts a plan view of an exemplary embodiment of a fluid infusion device suitable for use in the infusion system of FIG. 5.
Figure 7:
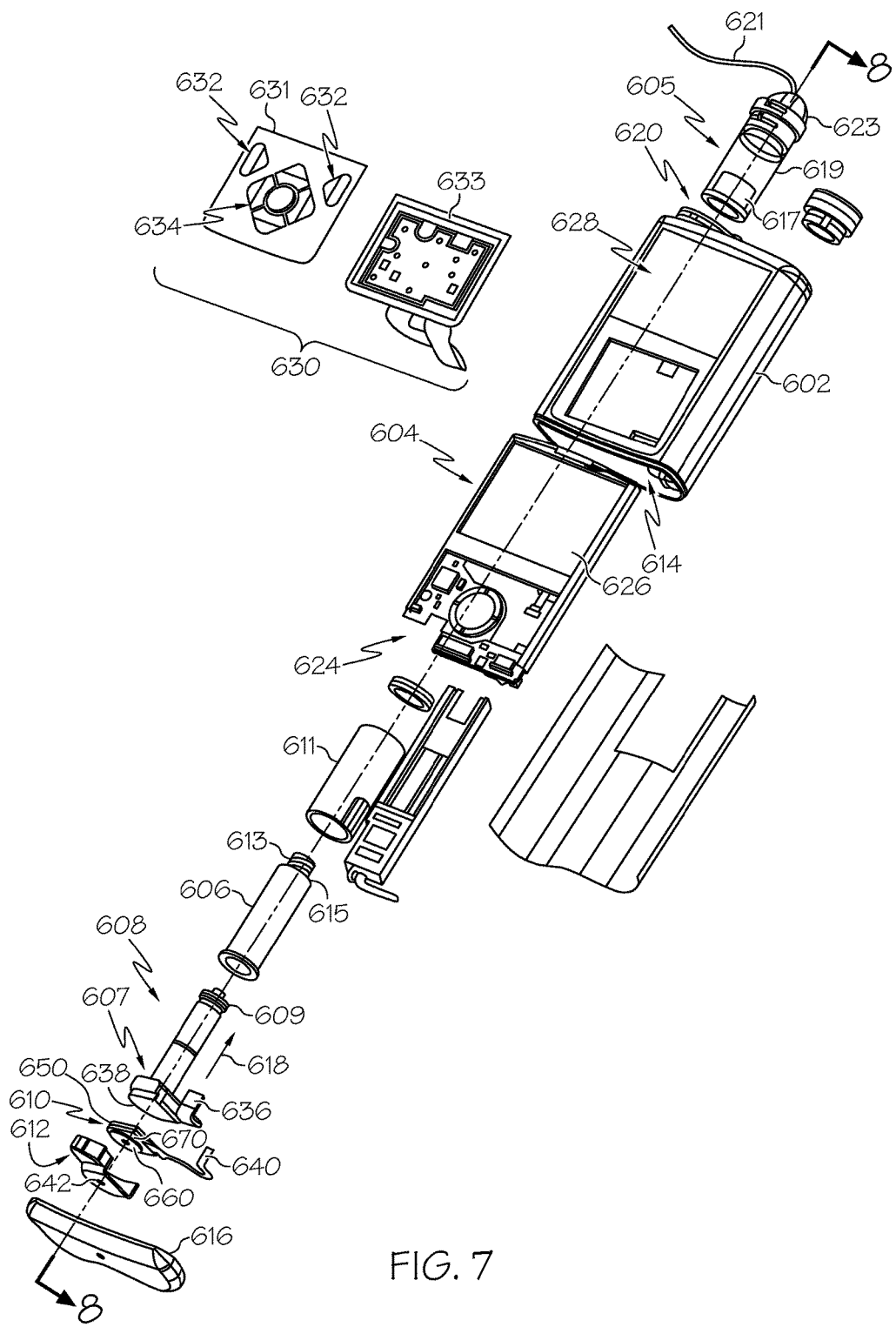
FIG. 7 is an exploded perspective view of the fluid infusion device of FIG. 6.
Figure 8:
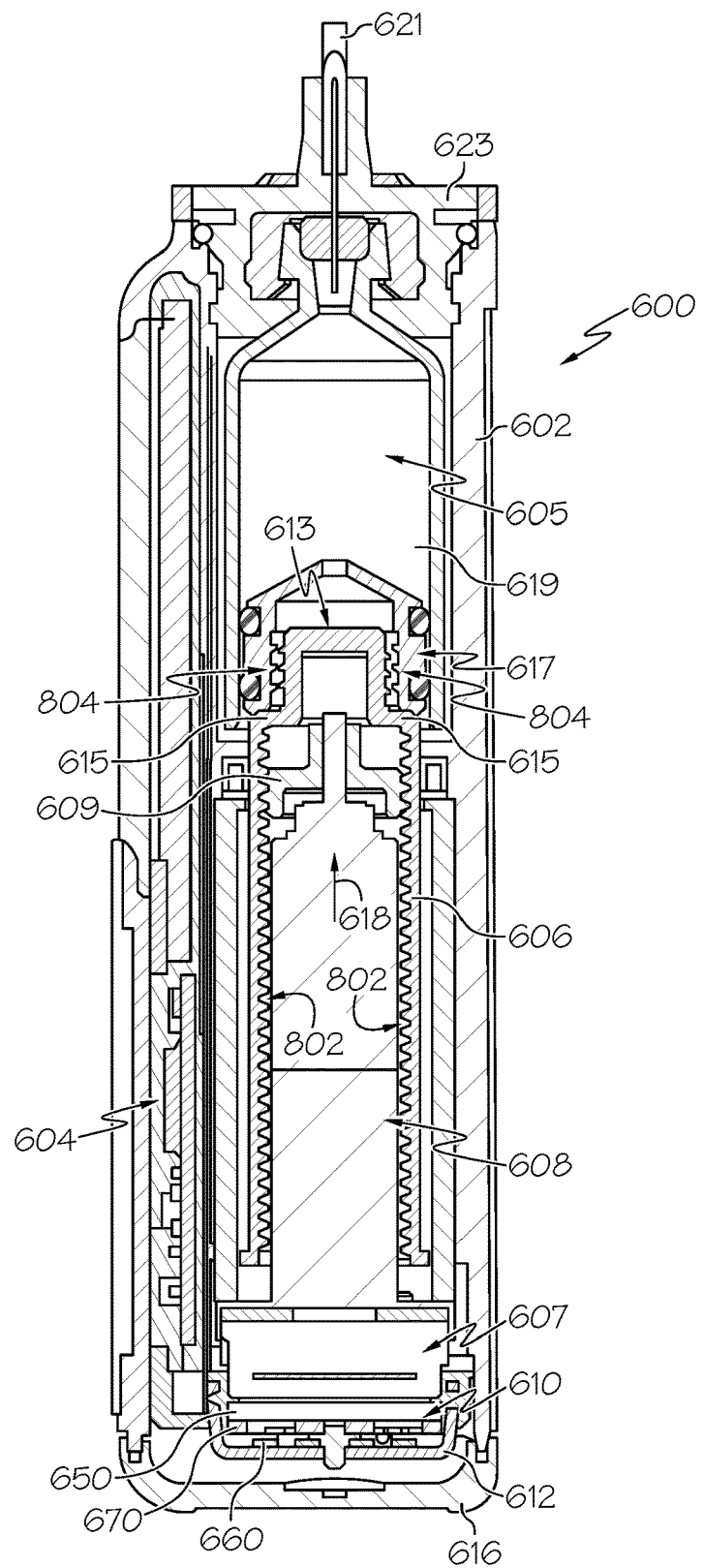
FIG. 8 is a cross-sectional view of the fluid infusion device of FIGS. 6-7 as viewed along line 8-8 in FIG. 7 when assembled with a reservoir inserted in the infusion device.

FIGS. 6-8 depict one exemplary embodiment of a fluid infusion device 600 (or alternatively, infusion pump) suitable for use in an infusion system, such as, for example, as infusion device 502 in the infusion system 500 of FIG. 5 or as infusion device 102 in the patient management system 100 of FIG. 1. The fluid infusion device 600 is a portable medical device designed to be carried or worn by a patient (or user), and the fluid infusion device 600 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 6-8 depict some aspects of the infusion device 600 in a simplified manner; in practice, the infusion device 600 could include additional elements, features, or components that are not shown or described in detail herein.

As best illustrated in FIGS. 6-7, the illustrated embodiment of the fluid infusion device 600 includes a housing 602 adapted to receive a fluid-containing reservoir 605. An opening 620 in the housing 602 accommodates a fitting 623 (or cap) for the reservoir 605, with the fitting 623 being configured to mate or otherwise interface with tubing 621 of an infusion set 625 that provides a fluid path to/from the body of the user. In this manner, fluid communication from the interior of the reservoir 605 to the user is established via the tubing 621. The illustrated fluid infusion device 600 includes a human-machine interface (HMI) 630 (or user interface) that includes elements 632, 634 that can be manipulated by the user to administer a bolus of fluid (e.g., insulin), to change therapy settings, to change user preferences, to select display features, and the like. The infusion device also includes a display element 626, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 602 is formed from a substantially rigid material having a hollow interior 1014 adapted to allow an electronics assembly 604, a sliding member (or slide) 606, a drive system 608, a sensor assembly 610, and a drive system capping member 612 to be disposed therein in addition to the reservoir 605, with the contents of the housing 602 being enclosed by a housing capping member 616. The opening 620, the slide 606, and the drive system 608 are coaxially aligned in an axial direction (indicated by arrow 618), whereby the drive system 608 facilitates linear displacement of the slide 606 in the axial direction 618 to dispense fluid from the reservoir 605 (after the reservoir 605 has been inserted into opening 620), with the sensor assembly 610 being configured to measure axial forces (e.g., forces aligned with the axial direction 618) exerted on the sensor assembly 610 responsive to operating the drive system 608 to displace the slide 606. In various embodiments, the sensor assembly 610 may be utilized to detect one or more of the following: an occlusion in a fluid path that slows, prevents, or otherwise degrades fluid delivery from the reservoir 605 to a user's body; when the reservoir 605 is empty; when the slide 606 is properly seated with the reservoir 605; when a fluid dose has been delivered; when the infusion pump 600 is subjected to shock or vibration; when the infusion pump 600 requires maintenance.

Depending on the embodiment, the fluid-containing reservoir 605 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 7-8, the reservoir 605 typically includes a reservoir barrel 619 that contains the fluid and is concentrically and/or coaxially aligned with the slide 606 (e.g., in the axial direction 618) when the reservoir 605 is inserted into the infusion pump 600. The end of the reservoir 605 proximate the opening 620 may include or otherwise mate with the fitting 623, which secures the reservoir 605 in the housing 602 and prevents displacement of the reservoir 605 in the axial direction 618 with respect to the housing 602 after the reservoir 605 is inserted into the housing 602. As described above, the fitting 623 extends from (or through) the opening 620 of the housing 602 and mates with tubing 621 to establish fluid communication from the interior of the reservoir 605 (e.g., reservoir barrel 619) to the user via the tubing 621 and infusion set 625. The opposing end of the reservoir 605 proximate the slide 606 includes a plunger 617 (or stopper) positioned to push fluid from inside the barrel 619 of the reservoir 605 along a fluid path through tubing 621 to a user. The slide 606 is configured to mechanically couple or otherwise engage with the plunger 617, thereby becoming seated with the plunger 617 and/or reservoir 605. Fluid is forced from the reservoir 605 via tubing 621 as the drive system 608 is operated to displace the slide 606 in the axial direction 618 toward the opening 620 in the housing 602.

In the illustrated embodiment of FIGS. 7-8, the drive system 608 includes a motor assembly 607 and a drive screw 609. The motor assembly 607 includes a motor that is coupled to drive train components of the drive system 608 that are configured to convert rotational motor motion to a translational displacement of the slide 606 in the axial direction 618, and thereby engaging and displacing the plunger 617 of the reservoir 605 in the axial direction 618. In some embodiments, the motor assembly 607 may also be powered to translate the slide 606 in the opposing direction (e.g., the direction opposite direction 618) to retract and/or detach from the reservoir 605 to allow the reservoir 605 to be replaced. In exemplary embodiments, the motor assembly 607 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 605.

As best shown in FIG. 8, the drive screw 609 mates with threads 802 internal to the slide 606. When the motor assembly 607 is powered and operated, the drive screw 609 rotates, and the slide 606 is forced to translate in the axial direction 618. In an exemplary embodiment, the infusion pump 600 includes a sleeve 611 to prevent the slide 606 from rotating when the drive screw 609 of the drive system 608 rotates. Thus, rotation of the drive screw 609 causes the slide 606 to extend or retract relative to the drive motor assembly 607. When the fluid infusion device is assembled and operational, the slide 606 contacts the plunger 617 to engage the reservoir 605 and control delivery of fluid from the infusion pump 600. In an exemplary embodiment, the shoulder portion 615 of the slide 606 contacts or otherwise engages the plunger 617 to displace the plunger 617 in the axial direction 618. In alternative embodiments, the slide 606 may include a threaded tip 613 capable of being detachably engaged with internal threads 804 on the plunger 617 of the reservoir 605, as described in detail in U.S. Pat. Nos. 6,248,093 and 6,485,465, which are incorporated by reference herein.

As illustrated in FIG. 7, the electronics assembly 604 includes control electronics 624 coupled to the display element 626, with the housing 602 including a transparent window portion 628 that is aligned with the display element 626 to allow the display 626 to be viewed by the user when the electronics assembly 604 is disposed within the interior 1014 of the housing 602. The control electronics 624 generally represent the hardware, firmware, processing logic and/or software (or combinations thereof) configured to control operation of the motor assembly 607 and/or drive system 608, as described in greater detail below in the context of FIG. 9. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 624 includes one or more programmable controllers that may be programmed to control operation of the infusion pump 600.

The motor assembly 607 includes one or more electrical leads 636 adapted to be electrically coupled to the electronics assembly 604 to establish communication between the control electronics 624 and the motor assembly 607. In response to command signals from the control electronics 624 that operate a motor driver (e.g., a power converter) to regulate the amount of power supplied to the motor from a power supply, the motor actuates the drive train components of the drive system 608 to displace the slide 606 in the axial direction 618 to force fluid from the reservoir 605 along a fluid path (including tubing 621 and an infusion set), thereby administering doses of the fluid contained in the reservoir 605 into the user's body. Preferably, the power supply is realized one or more batteries contained within the housing 602. Alternatively, the power supply may be a solar panel, capacitor, AC or DC power supplied through a power cord, or the like. In some embodiments, the control electronics 624 may operate the motor of the motor assembly 607 and/or drive system 608 in a stepwise manner, typically on an intermittent basis; to administer discrete precise doses of the fluid to the user according to programmed delivery profiles.

Referring to FIGS. 6-8, as described above, the user interface 630 includes HMI elements, such as buttons 632 and a directional pad 634, that are formed on a graphic keypad overlay 631 that overlies a keypad assembly 633, which includes features corresponding to the buttons 632, directional pad 634 or other user interface items indicated by the graphic keypad overlay 631. When assembled, the keypad assembly 633 is coupled to the control electronics 624, thereby allowing the HMI elements 632, 634 to be manipulated by the user to interact with the control electronics 624 and control operation of the infusion pump 600, for example, to administer a bolus of insulin, to change therapy settings, to change user preferences, to select display features, to set or disable alarms and reminders, and the like. In this regard, the control electronics 624 maintains and/or provides information to the display 626 regarding program parameters, delivery profiles, pump operation, alarms, warnings, statuses, or the like, which may be adjusted using the HMI elements 632, 634. In various embodiments, the HMI elements 632, 634 may be realized as physical objects (e.g., buttons, knobs, joysticks, and the like) or virtual objects (e.g., using touch-sensing and/or proximity-sensing technologies). For example, in some embodiments, the display 626 may be realized as a touch screen or touch-sensitive display, and in such embodiments, the features and/or functionality of the HMI elements 632, 634 may be integrated into the display 626 and the HMI 630 may not be present. In some embodiments, the electronics assembly 604 may also include alert generating elements coupled to the control electronics 624 and suitably configured to generate one or more types of feedback, such as, without limitation: audible feedback; visual feedback; haptic (physical) feedback; or the like.

Referring to FIGS. 7-8, in accordance with one or more embodiments, the sensor assembly 610 includes a back plate structure 650 and a loading element 660. The loading element 660 is disposed between the capping member 612 and a beam structure 670 that includes one or more beams having sensing elements disposed thereon that are influenced by compressive force applied to the sensor assembly 610 that deflects the one or more beams, as described in greater detail in U.S. Pat. No. 8,474,332, which is incorporated by reference herein. In exemplary embodiments, the back plate structure 650 is affixed, adhered, mounted, or otherwise mechanically coupled to the bottom surface 638 of the drive system 608 such that the back plate structure 650 resides between the bottom surface 638 of the drive system 608 and the housing cap 616. The drive system capping member 612 is contoured to accommodate and conform to the bottom of the sensor assembly 610 and the drive system 608. The drive system capping member 612 may be affixed to the interior of the housing 602 to prevent displacement of the sensor assembly 610 in the direction opposite the direction of force provided by the drive system 608 (e.g., the direction opposite direction 618). Thus, the sensor assembly 610 is positioned between the motor assembly 607 and secured by the capping member 612, which prevents displacement of the sensor assembly 610 in a downward direction opposite the direction of arrow 618, such that the sensor assembly 610 is subjected to a reactionary compressive force when the drive system 608 and/or motor assembly 607 is operated to displace the slide 606 in the axial direction 618 in opposition to the fluid pressure in the reservoir 605. Under normal operating conditions, the compressive force applied to the sensor assembly 610 is correlated with the fluid pressure in the reservoir 605. As shown, electrical leads 640 are adapted to electrically couple the sensing elements of the sensor assembly 610 to the electronics assembly 604 to establish communication to the control electronics 624, wherein the control electronics 624 are configured to measure, receive, or otherwise obtain electrical signals from the sensing elements of the sensor assembly 610 that are indicative of the force applied by the drive system 608 in the axial direction 618.

Figure 9:
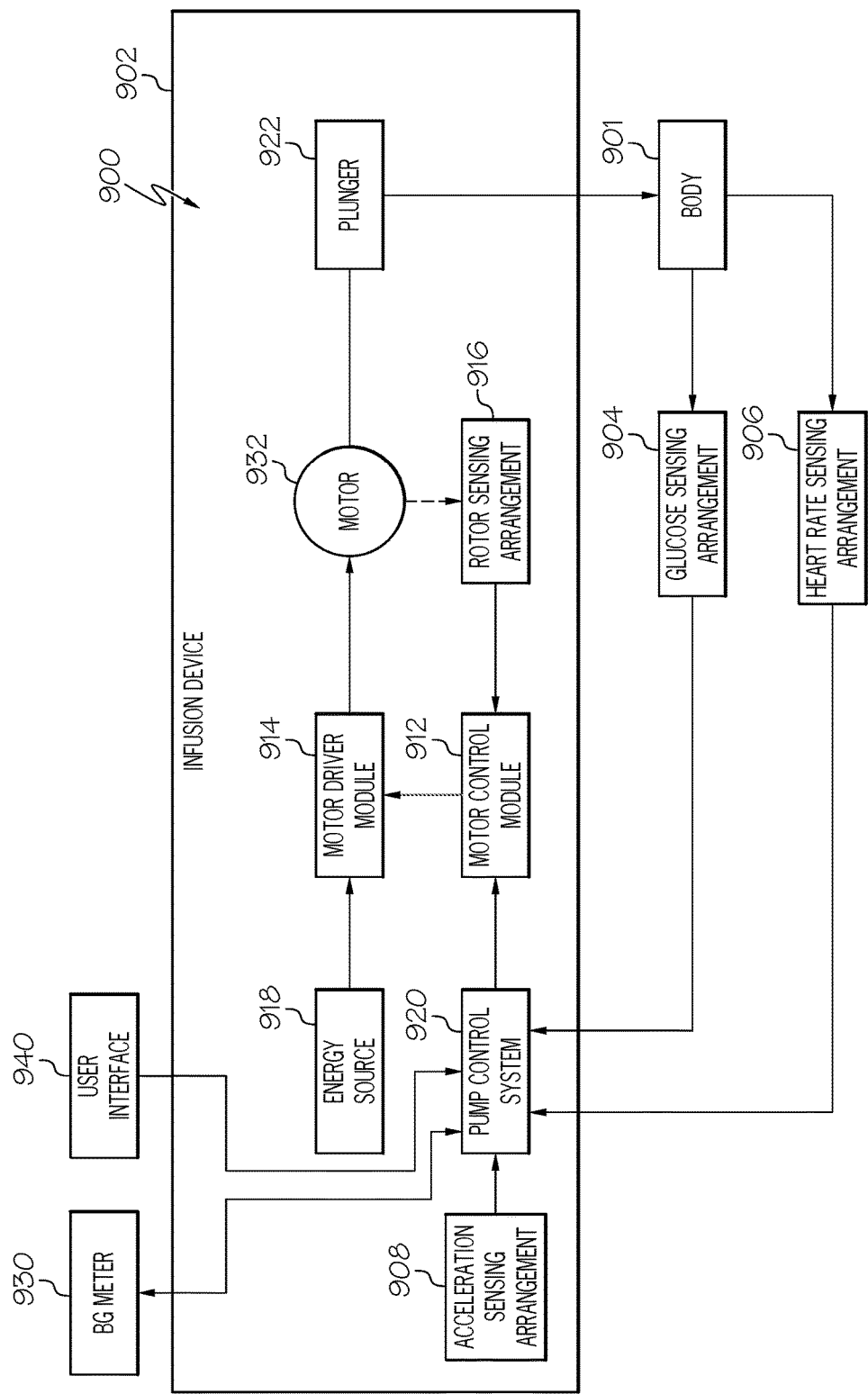
FIG. 9 is a block diagram of an exemplary control system suitable for use in a fluid infusion device in one or more embodiments.

FIG. 9 depicts an exemplary embodiment of a control system 900 suitable for use with an infusion device 902, such as any one of the infusion devices 102, 502, 600 described above. The control system 900 is capable of controlling or otherwise regulating a physiological condition in the body 901 of a user to a desired (or target) value or otherwise maintain the condition within a range of acceptable values in an automated or autonomous manner. In one or more exemplary embodiments, the condition being regulated is sensed, detected, measured or otherwise quantified by a sensing arrangement 904 (e.g., sensing arrangement 904) communicatively coupled to the infusion device 902. However, it should be noted that in alternative embodiments, the condition being regulated by the control system 900 may be correlative to the measured values obtained by the sensing arrangement 904. That said, for clarity and purposes of explanation, the subject matter may be described herein in the context of the sensing arrangement 904 being realized as a glucose sensing arrangement that senses, detects, measures or otherwise quantifies the user's glucose level, which is being regulated in the body 901 of the user by the control system 900.

In exemplary embodiments, the sensing arrangement 904 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 901 of the user. The output electrical signals are filtered or otherwise processed to obtain a measurement value indicative of the user's interstitial fluid glucose level. In exemplary embodiments, a blood glucose meter 930, such as a finger stick device, is utilized to directly sense, detect, measure or otherwise quantify the blood glucose in the body 901 of the user. In this regard, the blood glucose meter 930 outputs or otherwise provides a measured blood glucose value that may be utilized as a reference measurement for calibrating the sensing arrangement 904 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 904 may alternatively be referred to herein as the sensor glucose value, the sensed glucose value, or variants thereof.

In exemplary embodiments, the infusion system 900 also includes one or more additional sensing arrangements 906, 908 configured to sense, detect, measure or otherwise quantify a characteristic of the body 901 of the user that is indicative of a condition in the body 901 of the user. For example, in the illustrated embodiment, the infusion system 900 includes a heart rate sensing arrangement 906 that may be worn on or otherwise associated with the user's body 901 to sense, detect, measure or otherwise quantify the user's heart rate, which, in turn, may be indicative of exercise, stress, or some other condition in the body 901 that is likely to influence the user's insulin response in the body 901. The measured heart rate values output by the heart rate sensing arrangement 906 may be utilized to calculate or otherwise quantify one or more characteristics of the user's heart rate. In some embodiments, the heart rate measurement data from the heart rate sensing arrangement 906 is utilized by processes 200, 300 to develop a parameter model for calculating a current value of a parameter of interest for the user based at least in part on the current heart rate measurement value from the heart rate sensing arrangement 906. While the illustrated embodiment depicts the heart rate sensing arrangement 906 as being realized as a standalone component worn by the user, in alternative embodiments, the heart rate sensing arrangement 906 may be integrated with the infusion device 902 or with another sensing arrangement 904, 908 worn on the body 901 of the user.

Additionally, the illustrated infusion system 900 includes an acceleration sensing arrangement 908 (or accelerometer) that may be worn on or otherwise associated with the user's body 901 to sense, detect, measure or otherwise quantify an acceleration of the user's body 901, which, in turn, may be indicative of exercise or some other condition in the body 901 that is likely to influence the user's insulin response. In the illustrated embodiment, the acceleration sensing arrangement 908 is depicted as being integrated into the infusion device 902, however, in alternative embodiments, the acceleration sensing arrangement 908 may be integrated with another sensing arrangement 904, 906 on the body 901 of the user, or the acceleration sensing arrangement 908 may be realized as a standalone component that is worn by the user. The acceleration measurement data may be utilized to establish behavioral history of the user (e.g., when the user is exercising or awake versus at rest). In some embodiments, the acceleration measurement data from the acceleration sensing arrangement 908 is utilized by processes 200, 300 to develop a parameter model for calculating a current value of a parameter of interest for the user based at least in part on the current acceleration measurement value from the acceleration sensing arrangement 906 or other current behavior or activities correlative to the current acceleration measurement value.

In the illustrated embodiment, the pump control system 920 generally represents the electronics and other components of the infusion device 902 that control operation of the fluid infusion device 902 according to a desired infusion delivery program in a manner that is influenced by the sensed glucose value indicative of a current glucose level in the body 901 of the user. For example, to support a closed-loop operating mode, the pump control system 920 maintains, receives, or otherwise obtains a target or commanded glucose value, and automatically generates or otherwise determines dosage commands for operating an actuation arrangement, such as a motor 932, to displace the plunger 917 and deliver insulin to the body 901 of the user based on the difference between a sensed glucose value and the target glucose value. In other operating modes, the pump control system 920 may generate or otherwise determine dosage commands configured to maintain the sensed glucose value below an upper glucose limit, above a lower glucose limit, or otherwise within a desired range of glucose values. In practice, the infusion device 902 may store or otherwise maintain the target value, upper and/or lower glucose limit(s), and/or other glucose threshold value(s) in a data storage element accessible to the pump control system 920.

The target glucose value and other threshold glucose values may be received from an external component (e.g., CCD 506 and/or computing device 508) or be input by a user via a user interface element 940 associated with the infusion device 902. In practice, the one or more user interface element(s) 940 associated with the infusion device 902 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 940 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 9 depicts the user interface element(s) 940 as being separate from the infusion device 902, in practice, one or more of the user interface element(s) 940 may be integrated with the infusion device 902. Furthermore, in some embodiments, one or more user interface element(s) 940 are integrated with the sensing arrangement 904 in addition to and/or in alternative to the user interface element(s) 940 integrated with the infusion device 902. The user interface element(s) 940 may be manipulated by the user to operate the infusion device 902 to deliver correction boluses, adjust target and/or threshold values, modify the delivery control scheme or operating mode, and the like, as desired.

Still referring to FIG. 9, in the illustrated embodiment, the infusion device 902 includes a motor control module 912 coupled to a motor 932 (e.g., motor assembly 607) that is operable to displace a plunger 917 (e.g., plunger 617) in a reservoir (e.g., reservoir 605) and provide a desired amount of fluid to the body 901 of a user. In this regard, displacement of the plunger 917 results in the delivery of a fluid that is capable of influencing the condition in the body 901 of the user to the body 901 of the user via a fluid delivery path (e.g., via tubing 621 of an infusion set 625). A motor driver module 914 is coupled between an energy source 918 and the motor 932. The motor control module 912 is coupled to the motor driver module 914, and the motor control module 912 generates or otherwise provides command signals that operate the motor driver module 914 to provide current (or power) from the energy source 918 to the motor 932 to displace the plunger 917 in response to receiving, from a pump control system 920, a dosage command indicative of the desired amount of fluid to be delivered.

In exemplary embodiments, the energy source 918 is realized as a battery housed within the infusion device 902 (e.g., within housing 602) that provides direct current (DC) power. In this regard, the motor driver module 914 generally represents the combination of circuitry, hardware and/or other electrical components configured to convert or otherwise transfer DC power provided by the energy source 918 into alternating electrical signals applied to respective phases of the stator windings of the motor 932 that result in current flowing through the stator windings that generates a stator magnetic field and causes the rotor of the motor 932 to rotate. The motor control module 912 is configured to receive or otherwise obtain a commanded dosage from the pump control system 920, convert the commanded dosage to a commanded translational displacement of the plunger 917, and command, signal, or otherwise operate the motor driver module 914 to cause the rotor of the motor 932 to rotate by an amount that produces the commanded translational displacement of the plunger 917. For example, the motor control module 912 may determine an amount of rotation of the rotor required to produce translational displacement of the plunger 917 that achieves the commanded dosage received from the pump control system 920. Based on the current rotational position (or orientation) of the rotor with respect to the stator that is indicated by the output of the rotor sensing arrangement 916, the motor control module 912 determines the appropriate sequence of alternating electrical signals to be applied to the respective phases of the stator windings that should rotate the rotor by the determined amount of rotation from its current position (or orientation). In embodiments where the motor 932 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 912 operates the motor driver module 914 to apply the determined alternating electrical signals (e.g., the command signals) to the stator windings of the motor 932 to achieve the desired delivery of fluid to the user.

When the motor control module 912 is operating the motor driver module 914, current flows from the energy source 918 through the stator windings of the motor 932 to produce a stator magnetic field that interacts with the rotor magnetic field. In some embodiments, after the motor control module 912 operates the motor driver module 914 and/or motor 932 to achieve the commanded dosage, the motor control module 912 ceases operating the motor driver module 914 and/or motor 932 until a subsequent dosage command is received. In this regard, the motor driver module 914 and the motor 932 enter an idle state during which the motor driver module 914 effectively disconnects or isolates the stator windings of the motor 932 from the energy source 918. In other words, current does not flow from the energy source 918 through the stator windings of the motor 932 when the motor 932 is idle, and thus, the motor 932 does not consume power from the energy source 918 in the idle state, thereby improving efficiency.

Depending on the embodiment, the motor control module 912 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the motor control module 912 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 912. The computer-executable programming instructions, when read and executed by the motor control module 912, cause the motor control module 912 to perform or otherwise support the tasks, operations, functions, and processes described herein.

It should be appreciated that FIG. 9 is a simplified representation of the infusion device 902 for purposes of explanation and is not intended to limit the subject matter described herein in any way. In this regard, depending on the embodiment, some features and/or functionality of the sensing arrangement 904 may implemented by or otherwise integrated into the pump control system 920, or vice versa. Similarly, in practice, the features and/or functionality of the motor control module 912 may implemented by or otherwise integrated into the pump control system 920, or vice versa. Furthermore, the features and/or functionality of the pump control system 920 may be implemented by control electronics 624 located in the fluid infusion device 902, while in alternative embodiments, the pump control system 920 may be implemented by a remote computing device that is physically distinct and/or separate from the infusion device 902, such as, for example, the CCD 506 or the computing device 508.

Figure 10:
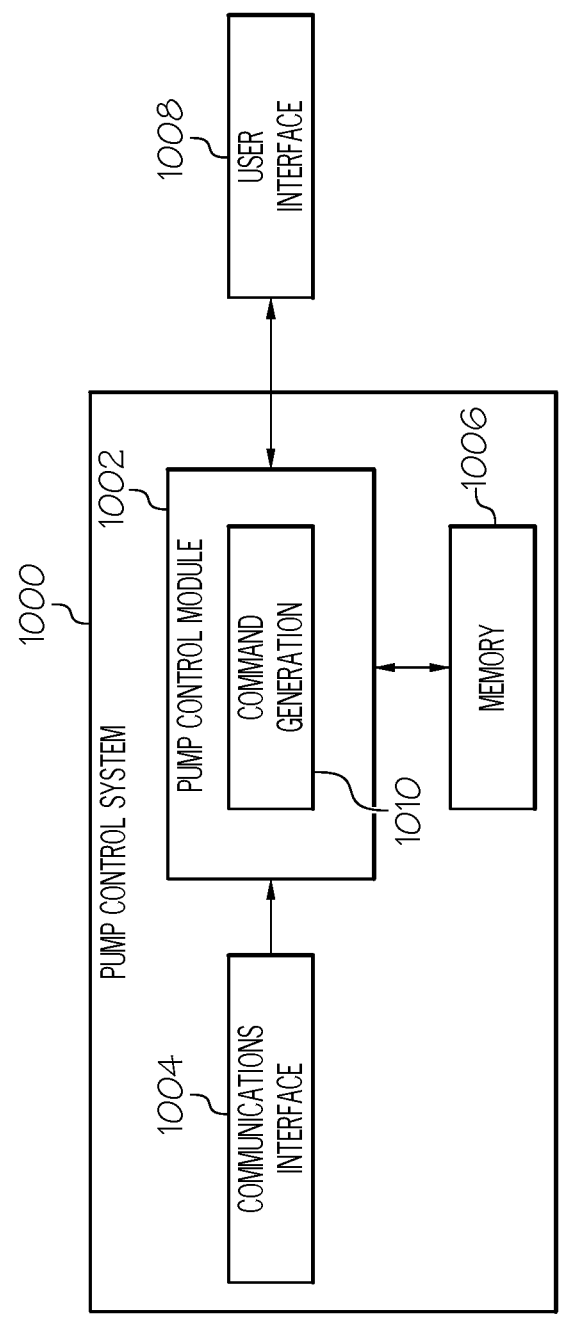
FIG. 10 is a block diagram of an exemplary pump control system suitable for use in the control system of FIG. 9 in one or more embodiments.

FIG. 10 depicts an exemplary embodiment of a pump control system 1000 suitable for use as the pump control system 920 in FIG. 9 in accordance with one or more embodiments. The illustrated pump control system 1000 includes, without limitation, a pump control module 1002, a communications interface 1004, and a data storage element (or memory) 1006. The pump control module 1002 is coupled to the communications interface 1004 and the memory 1006, and the pump control module 1002 is suitably configured to support the operations, tasks, and/or processes described herein. In exemplary embodiments, the pump control module 1002 is also coupled to one or more user interface elements 1008 (e.g., user interface 630, 940) for receiving user input and providing notifications, alerts, or other therapy information to the user. Although FIG. 10 depicts the user interface element 1008 as being separate from the pump control system 1000, in various alternative embodiments, the user interface element 1008 may be integrated with the pump control system 1000 (e.g., as part of the infusion device 902), the sensing arrangement 904 or another element of an infusion system 900 (e.g., the computer 508 or CCD 506).

Referring to FIG. 10 and with reference to FIG. 9, the communications interface 1004 generally represents the hardware, circuitry, logic, firmware and/or other components of the pump control system 1000 that are coupled to the pump control module 1002 and configured to support communications between the pump control system 1000 and the sensing arrangement 904. In this regard, the communications interface 1004 may include or otherwise be coupled to one or more transceiver modules capable of supporting wireless communications between the pump control system 920, 1000 and the sensing arrangement 104, 504, 904 or another electronic device 106, 110, 400, 412, 506, 508 in a system 100, 400, 500 including the infusion device 102, 502, 902. For example, the communications interface 1004 may be utilized to receive sensor measurement values or other measurement data from a sensing arrangement 104, 504, 904 as well as upload such sensor measurement values to a server 106 or other computing device 110, 400, 412, 508. In other embodiments, the communications interface 1004 may be configured to support wired communications to/from the sensing arrangement 904.

The pump control module 1002 generally represents the hardware, circuitry, logic, firmware and/or other component of the pump control system 1000 that is coupled to the communications interface 1004 and configured to determine dosage commands for operating the motor 932 to deliver fluid to the body 901 based on data received from the sensing arrangement 904 and perform various additional tasks, operations, functions and/or operations described herein. For example, in exemplary embodiments, pump control module 1002 implements or otherwise executes a command generation application 1010 that supports one or more autonomous operating modes and calculates or otherwise determines dosage commands for operating the motor 932 of the infusion device 902 in an autonomous operating mode based at least in part on a current measurement value for a condition in the body 901 of the user. For example, in a closed-loop operating mode, the command generation application 1010 may determine a dosage command for operating the motor 932 to deliver insulin to the body 901 of the user based at least in part on the current glucose measurement value most recently received from the sensing arrangement 904 to regulate the user's blood glucose level to a target reference glucose value. Additionally, the command generation application 1010 may generate dosage commands for boluses that are manually-initiated or otherwise instructed by a user via a user interface element 1008.

Still referring to FIG. 10, depending on the embodiment, the pump control module 1002 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the pump control module 1002, or in any practical combination thereof. In exemplary embodiments, the pump control module 1002 includes or otherwise accesses the data storage element or memory 1006, which may be realized using any sort of non-transitory computer-readable medium capable of storing programming instructions for execution by the pump control module 1002. The computer-executable programming instructions, when read and executed by the pump control module 1002, cause the pump control module 1002 to implement or otherwise generate the command generation application 1010 and perform tasks, operations, functions, and processes described herein.

It should be understood that FIG. 10 is a simplified representation of a pump control system 1000 for purposes of explanation and is not intended to limit the subject matter described herein in any way. For example, in some embodiments, the features and/or functionality of the motor control module 912 may be implemented by or otherwise integrated into the pump control system 1000 and/or the pump control module 1002, for example, by the command generation application 1010 converting the dosage command into a corresponding motor command, in which case, the separate motor control module 912 may be absent from an embodiment of the infusion device 902.

Figure 11:
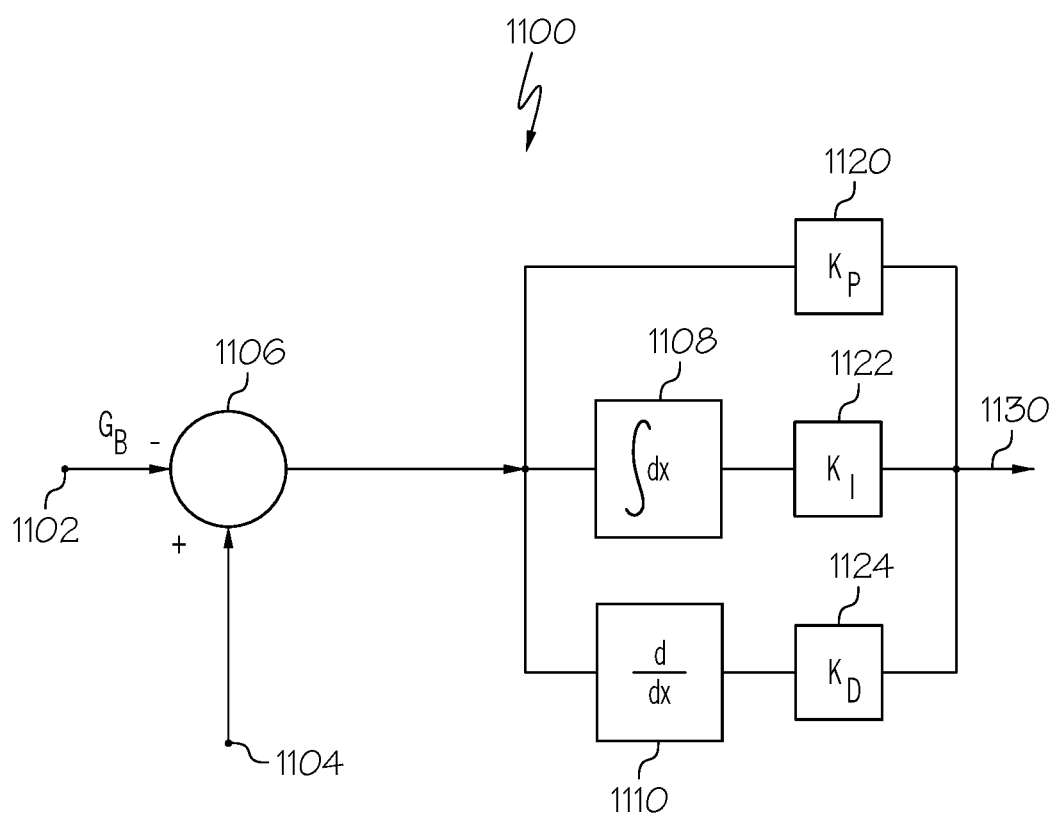
FIG. 11 is a block diagram of a closed-loop control system that may be implemented or otherwise supported by the pump control system in the fluid infusion device of FIGS. 9-10 in one or more exemplary embodiments.

FIG. 11 depicts an exemplary closed-loop control system 1100 that may be implemented by a pump control system 920, 1000 to provide a closed-loop operating mode that autonomously regulates a condition in the body of a user to a reference (or target) value. It should be appreciated that FIG. 11 is a simplified representation of the control system 1100 for purposes of explanation and is not intended to limit the subject matter described herein in any way.

In exemplary embodiments, the control system 1100 receives or otherwise obtains a target glucose value at input 1102. In some embodiments, the target glucose value may be stored or otherwise maintained by the infusion device 902 (e.g., in memory 1006), however, in some alternative embodiments, the target value may be received from an external component (e.g., CCD 506 and/or computer 508). In one or more embodiments, the target glucose value may be dynamically calculated or otherwise determined prior to entering the closed-loop operating mode based on one or more patient-specific control parameters. For example, the target blood glucose value may be calculated based at least in part on a patient-specific reference basal rate and a patient-specific daily insulin requirement, which are determined based on historical delivery information over a preceding interval of time (e.g., the amount of insulin delivered over the preceding 24 hours). The control system 1100 also receives or otherwise obtains a current glucose measurement value (e.g., the most recently obtained sensor glucose value) from the sensing arrangement 904 at input 1104. The illustrated control system 1100 implements or otherwise provides proportional-integral-derivative (PID) control to determine or otherwise generate delivery commands for operating the motor 910 based at least in part on the difference between the target glucose value and the current glucose measurement value. In this regard, the PID control attempts to minimize the difference between the measured value and the target value, and thereby regulates the measured value to the desired value. PID control parameters are applied to the difference between the target glucose level at input 1102 and the measured glucose level at input 1104 to generate or otherwise determine a dosage (or delivery) command provided at output 1130. Based on that delivery command, the motor control module 912 operates the motor 910 to deliver insulin to the body of the user to influence the user's glucose level, and thereby reduce the difference between a subsequently measured glucose level and the target glucose level.

The illustrated control system 1100 includes or otherwise implements a summation block 1106 configured to determine a difference between the target value obtained at input 1102 and the measured value obtained from the sensing arrangement 904 at input 1104, for example, by subtracting the target value from the measured value. The output of the summation block 1106 represents the difference between the measured and target values, which is then provided to each of a proportional term path, an integral term path, and a derivative term path. The proportional term path includes a gain block 1120 that multiplies the difference by a proportional gain coefficient, $K_P$, to obtain the proportional term. The integral term path includes an integration block 1108 that integrates the difference and a gain block 1122 that multiplies the integrated difference by an integral gain coefficient, $K_I$, to obtain the integral term. The derivative term path includes a derivative block 1110 that determines the derivative of the difference and a gain block 1124 that multiplies the derivative of the difference by a derivative gain coefficient, $K_D$, to obtain the derivative term. The proportional term, the integral term, and the derivative term are then added or otherwise combined to obtain a delivery command that is utilized to operate the motor at output 1130. Various implementation details pertaining to closed-loop PID control and determine gain coefficients are described in greater detail in U.S. Pat. No. 7,402,153, which is incorporated by reference.

In one or more exemplary embodiments, the PID gain coefficients are user-specific (or patient-specific) and dynamically calculated or otherwise determined prior to entering the closed-loop operating mode based on historical insulin delivery information (e.g., amounts and/or timings of previous dosages, historical correction bolus information, or the like), historical sensor measurement values, historical reference blood glucose measurement values, user-reported or user-input events (e.g., meals, exercise, and the like), and the like. In this regard, one or more patient-specific control parameters (e.g., an insulin sensitivity factor, a daily insulin requirement, an insulin limit, a reference basal rate, a reference fasting glucose, an active insulin action duration, pharmodynamical time constants, or the like) may be utilized to compensate, correct, or otherwise adjust the PID gain coefficients to account for various operating conditions experienced and/or exhibited by the infusion device 902. The PID gain coefficients may be maintained by the memory 1006 accessible to the pump control module 1002. In this regard, the memory 1006 may include a plurality of registers associated with the control parameters for the PID control. For example, a first parameter register may store the target glucose value and be accessed by or otherwise coupled to the summation block 1106 at input 1102, and similarly, a second parameter register accessed by the proportional gain block 1120 may store the proportional gain coefficient, a third parameter register accessed by the integration gain block 1122 may store the integration gain coefficient, and a fourth parameter register accessed by the derivative gain block 1124 may store the derivative gain coefficient.

Referring to FIGS. 9-11, in one or more embodiments, the parameter determination process 300 may be performed to calculate a value for a control parameter that influences operation of the infusion device 902 to deliver fluid to the patient. For example, in one embodiment one or more of the PID gain coefficients 1120, 1122, 1124 may be calculated or determined using a patient-specific model derived by the patient modeling process 200, or alternatively, may be adjusted or scaled using an adjustment factor that is calculated or determined using a patient-specific model derived by the patient modeling process 200. In other embodiments, the parameter determination process 300 may be performed to calculate a calibration factor value, an offset value, or another parameter value that influences the calibrated sensor glucose measurement value provided at input 1104, which, in turn, influences the delivery commands generated by the control system 1100, and thereby, the rate or amount of fluid delivered. Patient-specific models may also be used to determine delivery thresholds (e.g., to suspend, resume or otherwise modify delivery), alerting thresholds, or the like, which, in turn, influence the operation or behavior of the infusion device 902. Again, it should be noted that the processes 200, 300 may be utilized to calculate, adjust, modify, or otherwise determine any number of different potential control parameters utilized by the pump control module 920, 1002 and/or the control scheme implemented thereby based on the current values for any number of different predictive variables. In some embodiments, one or more patient-specific parameter models are stored or otherwise maintained by the pump control system 920, 1000 (e.g., in memory 1006) to support the infusion device 902 performing the parameter determination process 300 substantially in real-time.

Figure 12:
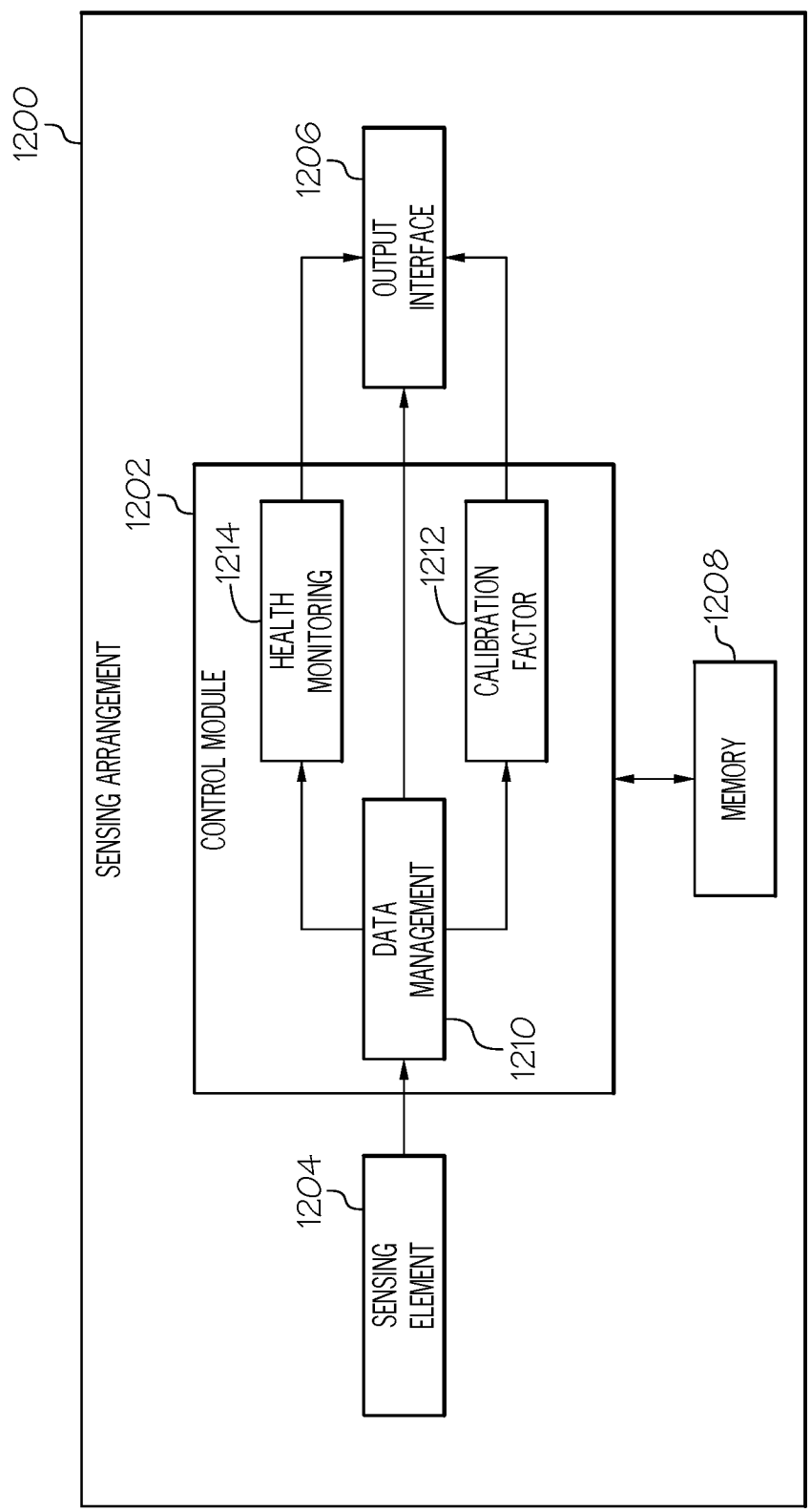
FIG. 12 is a block diagram of an electronic device suitable for use as a sensing arrangement or sensing device in any of the systems of FIG. 1, 5 or 9 in one or more exemplary embodiments.

FIG. 12 depicts an exemplary embodiment of an electronic device 1200 suitable for use as a sensing arrangement 104, 504, 904 in accordance with one or more embodiments. For purposes of explanation, but without limitation, the device 1200 may alternatively be referred to herein as a sensing device or a sensing arrangement. The illustrated sensing device 1200 includes, without limitation, a control module 1202, a sensing element 1204, an output interface 1206, and a data storage element (or memory) 1208. The control module 1202 is coupled to the sensing element 1204, the output interface 1206, and the memory 1208, and the control module 1202 is suitably configured to support the operations, tasks, and/or processes described herein.

The sensing element 1204 generally represents the component of the sensing device 1200 that is configured to generate, produce, or otherwise output one or more electrical signals indicative of a condition that is sensed, measured, or otherwise quantified by the sensing device 1200. In this regard, the physiological condition of a user influences a characteristic of the electrical signal output by the sensing element 1204, such that the characteristic of the output signal corresponds to or is otherwise correlative to the physiological condition that the sensing element 1204 is sensitive to. For example, the sensing element 1204 may be realized as a glucose sensing element that generates an output electrical signal having a current (or voltage) associated therewith that is correlative to the interstitial fluid glucose level that is sensed or otherwise measured in the body of the user by the sensing arrangement 1200. One or more glucose independent diagnostic signals or values associated with the sensing element 1204 may also be obtained by the sensing device 1200 and stored and/or transmitted by the sensing device 1200, such as, for example, electrochemical impedance spectroscopy (EIS) values or other measurements indicative of a characteristic impedance associated with the sensing element 1204.

Still referring to FIG. 12, the control module 1202 generally represents the hardware, circuitry, logic, firmware and/or other component(s) of the sensing device 1200 that is coupled to the sensing element 1204 to receive the electrical signals output by the sensing element 1204 and perform various additional tasks, operations, functions and/or processes described herein. For example, in one or more embodiments, the control module 1202 implements or otherwise executes a data management application module 1210 that filters, analyzes or otherwise processes the electrical signals received from the sensing element 1204 to obtain a filtered measurement value indicative of the measured interstitial fluid glucose level. In some embodiments, data management application module 1210 may add or subtract an offset to/from the measured electrical signal, as described above. In the illustrated embodiment, a calibration application module 1212 utilizes a calibration factor value to convert the filtered measurement value from the data management application 1210 to a calibrated sensed glucose value (or sensor glucose value). In some embodiments, the control module 1202 also implements or otherwise executes a health monitoring application module 1214 that detects or otherwise identifies replacement or other maintenance with respect to the sensing element 1204 is desirable.

Depending on the embodiment, the control module 1202 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 1202, or in any practical combination thereof.

In some embodiments, the control module 1202 includes an analog-to-digital converter (ADC) or another similar sampling arrangement that samples or otherwise converts the output electrical signal received from the sensing element 1204 into a corresponding digital measurement data value. In other embodiments, the sensing element 1204 may incorporate an ADC and output a digital measurement value. For purposes of explanation, the input to the data management application 1210 from the sensing element 1204 may alternatively be referred to herein as the unfiltered measurement value, which should be understood as referring to the digital value correlative to the interstitial fluid glucose level sensed by the sensing element 1204. In one or more embodiments, the current of the electrical signal output by the sensing element 1204 is influenced by the user's interstitial fluid glucose level, and the input to the data management application 1210 is realized as an unfiltered current measurement value (or unfiltered current measurement signal). As described above, depending on the embodiment, the unfiltered measurement value may be output directly by the sensing element 1204 or converted based on an analog electrical output signal from the sensing element 1204 by an ADC of the control module 1202.

In exemplary embodiments, the control module 1202 includes or otherwise accesses the data storage element or memory 1208. The memory 1208 may be realized using any sort of RAM, ROM, flash memory, registers, hard disks, removable disks, magnetic or optical mass storage, short or long term storage media, or any other non-transitory computer-readable medium capable of storing programming instructions, code, or other data for execution by the control module 1202. The computer-executable programming instructions, when read and executed by the control module 1202, cause the control module 1202 to implement or otherwise generate the applications 1210, 1212, 1214 and perform the tasks, operations, functions, and processes described in greater detail below.

The output interface 1206 generally represents the hardware, circuitry, logic, firmware and/or other components of the sensing device 1200 that are coupled to the control module 1202 for outputting data and/or information from/to the sensing device 1200 to/from the infusion device 902, the pump control system 920, the remote device 106, the client device 110 and/or the user. In this regard, in exemplary embodiments, the output interface 1206 is realized as a communications interface configured to support communications to/from the sensing device 1200. In such embodiments, the communications interface 1206 may include or otherwise be coupled to one or more transceiver modules capable of supporting wireless communications between the sensing device 1200 and another electronic device (e.g., an infusion device 502, 902 or another electronic device 506, 508 in an infusion system 500). Alternatively, the communications interface 1206 may be realized as a port that is adapted to receive or otherwise be coupled to a wireless adapter that includes one or more transceiver modules and/or other components that support the operations of the sensing device 1200 described herein. In other embodiments, the communications interface 1206 may be configured to support wired communications to/from the sensing device 1200. In yet other embodiments, the output interface 1206 may include or otherwise be realized as an output user interface element, such as a display element (e.g., a light-emitting diode or the like), a display device (e.g., a liquid crystal display or the like), a speaker or another audio output device, a haptic feedback device, or the like, for providing notifications or other information to the user. In such embodiments, the output user interface 1206 may be integrated with the sensing arrangement 904, 1200 (e.g., within a common housing) or implemented separately (e.g., user interface element 940).

It should be understood that FIG. 12 is a simplified representation of a sensing device 1200 for purposes of explanation and is not intended to limit the subject matter described herein in any way. In this regard, although FIG. 12 depicts the various elements residing within the sensing device 1200, one or more elements of the sensing device 1200 may be distinct or otherwise separate from the other elements of the sensing device 1200. For example, the sensing element 1204 may be separate and/or physically distinct from the control module 1202 and/or the communications interface 1206. Furthermore, although FIG. 12 depicts the applications 1210, 1212, 1214 as being implemented by the sensing device 1200, in alternative embodiments, features and/or functionality of one or more of the applications 1210, 1212, 1214 may be implemented by or otherwise reside on the infusion device 502, 902 or another device 506, 508 within an infusion system 500. For example, in some embodiments, the features and/or functionality of one or more of the applications 1210, 1212, 1214 may be implemented by the pump control system 920.

In one or more embodiments, the parameter determination process 300 may be performed to influence the output of the sensing device 1200. For example, as described above, an offset value applied by the data management module 1210 and/or a calibration factor value applied by the calibration factor module 1212 may be calculated or determined using a patient-specific model for the respective parameter derived by the patient modeling process 200, or alternatively, may be adjusted or scaled using an adjustment factor that is calculated or determined using a patient-specific model derived by the patient modeling process 200. Thus, the resulting calibrated sensor glucose measurement value provided to the output interface 1206 and output by the sensing device 1200 may be influenced by a patient-specific parameter module as described above. In other embodiments, a remaining usage life model may be utilized by the health monitoring module 1214 to calculate or otherwise determine a remaining usage life and provide a corresponding indication to the patient via the output interface 1206. In yet other embodiments, the health monitoring module 1214 may provide site rotation recommendations or other guidance to the patient via the output interface 1206 based on one or more parameter values calculated using a patient-specific parameter model. Again, it should be noted that the processes 200, 300 may be utilized to calculate, adjust, modify, or otherwise determine any number of different potential parameters utilized by the sensing device 1200 based on the current values for any number of different predictive variables. In some embodiments, one or more patient-specific parameter models are stored or otherwise maintained by the sensing device 1200 (e.g., in memory 1208) to support the sensing device 1200 performing the parameter determination process 300 substantially in real-time to dynamically adjust the value for one or more parameters.

It should be noted that although the subject matter may be described herein primarily in the context of an infusion device delivering insulin to the body of a patient with diabetes to regulate the patient's glucose level for purposes of explanation, in practice, the subject matter is not limited to use with infusion devices, insulin, diabetes or glucose control, and the like. Rather, the subject matter may be implemented in an equivalent manner in the context of patient management systems that do not include an infusion device, for example, in systems with where patients self-administer injections, oral medications, or the like, in systems where a sensing arrangement is utilized to monitor any a physiological condition of a patient in a substantially continuous manner, or in the context of a patient with dysglycemia or another physiological condition being monitored that is influenced by meals or other behavioral events. Thus, the infusion device 102 may be absent from some embodiments of the patient management system 100, in which case, the sensing arrangement 104 communicates with the server 106 and/or the client device 110 without reliance on the infusion device 102 as an intermediary.

In one or more exemplary embodiments, the subject matter described herein is implemented in the context of operating a sensing device 104, 1200 associated with a patient. In such embodiments, a control module 1202 of the sensing device 104, 1200 obtains current operational context information associated with the sensing device, obtains a parameter model associated with the patient (e.g., from database 108 via the server 106 and network 114), calculates a current parameter value based on the parameter model and the current operational context information, obtains one or more signals from a sensing element 1204 configured to measure a condition in a body of the patient, and provides an output, such as a calibrated measurement value, a user notification or alert, or the like, which is influenced by the calculated current parameter value and the one or more signals.

In yet other embodiments, the subject matter described herein is implemented in the context of another electronic device in a patient management system 100, such as a remote device 106, a client device 110, or an infusion device 102, to develop a patient-specific model for a parameter of interest. In such embodiments, the respective device 102, 106, 110 obtains historical measurements of a condition in a body of the patient previously provided by a sensing device 104, historical delivery information for fluid previously delivered to the body of the patient by the infusion device 102, historical operational context information associated with preceding operation of one or more of the infusion device 102 and the sensing device 104, and historical values for a parameter from one or more of the infusion device 102 and the sensing device 104. A patient-specific model of the parameter of interest is determined based on relationships between the historical measurements, the historical delivery information, the historical operational context information and the historical values, and the patient-specific model is provided to one of the infusion device 102, the sensing device 104 or the client device 110, wherein subsequent operation of that respective device is influenced by the patient-specific model. For example, the patient-specific model may influence alerts, guidance, recommendations or other notifications generated by the respective device, or other outputs generated by the respective device, such as, for example, measurement values, fluid deliveries, and the like.

For the sake of brevity, conventional techniques related to glucose sensing and/or monitoring, glucose regulation, modeling, machine learning, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not necessarily limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. A method of operating a sensing device associated with a patient, the sensing device including a control module coupled to a sensing element configured to measure a physiological condition in a body of the patient, the method comprising:
   obtaining, by the control module of the sensing device, current operational context information associated with the sensing device;
   obtaining, by the control module, an expected calibration factor parameter model associated with the patient;
   calculating, by the control module, an expected calibration factor value based on the expected calibration factor parameter model and the current operational context information;
   obtaining, by the control module, one or more electrical signals from the sensing element of the sensing device, the one or more electrical signals having a signal characteristic indicative of the physiological condition in the body of the patient;
   converting, by the control module, the one or more electrical signals into a calibrated measurement value for the physiological condition in the body of the patient using the expected calibration factor value; and
   outputting, by the control module, the calibrated measurement value for the physiological condition in the body of the patient.

2. The method of claim 1, wherein outputting the calibrated measurement value comprises transmitting the calibrated measurement value to an infusion device, wherein the infusion device is autonomously operated to deliver fluid to the body of the patient based on a difference between the calibrated measurement value and a reference value.

3. The method of claim 1, further comprising:
   obtaining historical operational context information associated with preceding operation of the sensing device;
   obtaining historical values for a calibration factor associated with the preceding operation of the sensing device; and
   determining the expected calibration factor model associated with the patient based on the historical operational context information and the historical values.

4. The method of claim 3, wherein:
   determining the expected calibration factor model comprises:
      identifying a subset of predictive variables from among the historical operational context information based on a correlation between the subset of predictive variables and the historical values for the calibration factor;
      determining the expected calibration factor model as a function of the subset of predictive variables based on historical values for the subset of predictive variables and the historical values for the calibration factor;

the current operational context information includes current values for the subset of predictive variables; and calculating the expected calibration factor value comprises calculating the expected calibration factor value as the function of the current values for the subset of predictive variables according to the expected calibration factor model.

5. The method of claim 4, wherein outputting the calibrated measurement value comprises transmitting the calibrated measurement value to an infusion device, wherein the infusion device is autonomously operated to deliver fluid to the body of the patient based on a difference between the calibrated measurement value and a reference value.

6. The method of claim 1, further comprising:
obtaining a measurement offset model associated with the patient;
calculating an expected offset value based on the current operational context information using the measurement offset model; and
subtracting the expected offset value from the one or more electrical signals prior to converting the one or more electrical signals into the calibrated measurement value.

7. The method of claim 6, wherein converting the one or more electrical signals into the calibrated measurement value comprises multiplying one or more results of subtracting the expected offset value from the one or more electrical signals by the expected calibration factor value.

8. The method of claim 7, further comprising:
obtaining historical operational context information associated with preceding operation of the sensing device;
obtaining historical values for a calibration factor associated with the preceding operation of the sensing device;
obtaining historical values for a measurement offset associated with the preceding operation of the sensing device; and
determining the expected calibration factor model associated with the patient based on the historical operational context information and the historical values for the calibration factor; and
determining the measurement offset model associated with the patient based on the historical operational context information and the historical values for the measurement offset.

9. The method of claim 1, further comprising generating a user notification based at least in part on the expected calibration factor value.

10. The method of claim 9, further comprising determining a remaining usage life associated with the sensing device based at least in part on the expected calibration factor value, wherein generating the user notification comprises providing an indication of the remaining usage life.

11. The method of claim 9, further comprising determining an optimal calibration time based at least in part on the expected calibration factor value, wherein generating the user notification comprises providing an indication of the optimal calibration time.

12. The method of claim 9, further comprising determining a recommended sensor site location based at least in part on the expected calibration factor value, wherein generating the user notification comprises providing an indication of the recommended sensor site location.

13. A non-transitory computer-readable medium having instructions stored thereon that are executable by the control module of the sensing device to perform the method of claim 1.

14. A sensing device comprising:
a sensing element to output one or more electrical signals having a signal characteristic indicative of a physiological condition in a body of a patient;
a data storage element to store an expected calibration factor parameter model associated with the patient;
an output interface; and
a control module coupled to the sensing element, the data storage element, and the output interface to calculate an expected calibration factor value based on the expected calibration factor parameter model and current operational context information, convert the one or more electrical signals into a calibrated measurement value for the physiological condition in the body of the patient using the expected calibration factor value, and provide the calibrated measurement value at the output interface.

15. The sensing device of claim 14, wherein:
the output interface comprises a communications interface to transmit the calibrated measurement value to an infusion device; and
operation of the infusion device to regulate the physiological condition of the patient based on the calibrated measurement value.

16. The sensing device of claim 14, wherein:
the output interface comprises an output user interface element; and
the output comprises a user notification generated based at least in part on the expected calibration factor value.

17. The sensing device of claim 16, wherein:
the control module determines a remaining usage life associated with the sensing device based at least in part on the expected calibration factor value; and
the user notification comprises an indication of the remaining usage life.

18. A system comprising:
a computing device communicatively coupled to a network to obtain historical operational context information associated with a patient via the network, obtain historical values for a calibration factor associated with the patient via the network, and determine a patient-specific model for the calibration factor based on a relationship between the historical operational context information and the historical values; and
a sensing device communicatively coupled to the computing device to obtain the patient-specific model, obtain current operational context information associated with the sensing device, calculate an expected value for the calibration factor based on the patient-specific model and the current operational context information, obtain one or more electrical signals having a signal characteristic indicative of a physiological condition in a body of the patient from a sensing element of the sensing device, convert the one or more electrical signals into a calibrated measurement value for the physiological condition in the body of the patient using the expected value for the calibration factor, and output the calibrated measurement value.

19. The system of claim 18, further comprising an infusion device coupled to the sensing device, wherein:
the infusion device is operable to deliver fluid to the body of the patient based on the calibrated measurement value.

20. The method of claim 1, wherein:
the current operational context comprises a current sensor site location on the body of the patient; and
calculating the expected calibration factor value comprises determining the expected calibration factor value as a function of the current sensor site location.

* * * * *